United States Patent
Tang et al.

(10) Patent No.: US 10,195,570 B2
(45) Date of Patent: Feb. 5, 2019

(54) FABRICATION OF MICROFILTERS AND NANOFILTERS AND THEIR APPLICATIONS

(75) Inventors: Cha-Mei Tang, Potomac, MD (US); Olga Makarova, Naperville, IL (US)

(73) Assignee: Creative Micro Tech, Inc., Potomac, MD (US)

( * ) Notice: Subject to any disclaimer, the term of this patent is extended or adjusted under 35 U.S.C. 154(b) by 447 days.

(21) Appl. No.: 13/345,538

(22) Filed: Jan. 6, 2012

(65) Prior Publication Data

US 2012/0183946 A1 Jul. 19, 2012

Related U.S. Application Data

(60) Provisional application No. 61/430,818, filed on Jan. 7, 2011.

(51) Int. Cl.
*C03C 15/00* (2006.01)
*C03C 25/68* (2006.01)
(Continued)

(52) U.S. Cl.
CPC ........... *B01D 67/0034* (2013.01); *A61M 1/34* (2013.01); *B01D 67/0027* (2013.01); *B01D 67/0088* (2013.01); *B01D 69/12* (2013.01); *B01D 71/46* (2013.01); *B01D 71/64* (2013.01); *C12M 47/02* (2013.01); *B01D 61/147* (2013.01); *B01D 2323/34* (2013.01); *B01D 2325/02* (2013.01);
(Continued)

(58) Field of Classification Search
CPC ............... G01N 1/4077; G01N 2001/4088
USPC .................................................. 216/58, 83
See application file for complete search history.

(56) References Cited

U.S. PATENT DOCUMENTS

| | | |
|---|---|---|
| 4,454,749 A | 6/1984 | Guillemin et al. |
| 4,777,021 A | 10/1988 | Wertz et al. |

(Continued)

FOREIGN PATENT DOCUMENTS

| | | |
|---|---|---|
| EP | 1031371 A1 | 8/2000 |
| GB | 2392854 A | 3/2004 |
| JP | 58-68899 U | 5/1983 |

OTHER PUBLICATIONS

"DuPont PerMX 3020 dryfilm resist _ 4m-association" (web page), 2008.*

*Primary Examiner* — Thomas T Pham
(74) *Attorney, Agent, or Firm* — Dickinson Wright, PLLC

(57) ABSTRACT

Micro- and nanofilters with precision pore sizes and pore layout have applications in many fields including capturing circulating tumor cells and fetal cells in blood, water treatment, pathogen detection in water, etc. Methods to fabricate micro- and nanofilters not using track etching or reactive ion etching are provided, allowing easy fabrication of single layer or stack of films simultaneously, and/or stack of films on rolls. Microfilter can be made using one or more layers of material. Invention enables mass production of microfilters with lithographic quality at low cost. Isolation, enumeration and characterization of circulating tumor cells using microfilters provides (i) guides to cancer treatment selection and personalize dosage, (ii) low cost monitoring for treatment response, disease progression and recurrence, (iii) assessment of pharmacodynamic effects, (iv) information on mechanisms of resistance to therapy, and (v) cancer staging. Microfabrication methods are also applicable to fabrication of any free standing patterned polymeric films.

13 Claims, 26 Drawing Sheets

(51) Int. Cl.
  B01D 67/00 (2006.01)
  A61M 1/34 (2006.01)
  B01D 69/12 (2006.01)
  C12M 1/00 (2006.01)
  B01D 71/46 (2006.01)
  B01D 71/64 (2006.01)
  B01D 61/14 (2006.01)
  G01N 21/64 (2006.01)
  G03F 7/20 (2006.01)

(52) U.S. Cl.
  CPC ...... *B01D 2325/08* (2013.01); *G01N 21/6428* (2013.01); *G03F 7/2022* (2013.01); *Y10T 428/249978* (2015.04)

(56) References Cited

U.S. PATENT DOCUMENTS

| | | | |
|---|---|---|---|
| 4,783,318 A | 11/1988 | Lapakko | |
| 4,840,698 A * | 6/1989 | Kuehnert | 156/485 |
| 5,116,724 A | 5/1992 | Delaage et al. | |
| 5,221,483 A | 6/1993 | Glenn et al. | |
| 5,753,014 A * | 5/1998 | Van Rijn | B01D 39/1692 55/524 |
| 5,916,626 A * | 6/1999 | Moon | C23C 16/30 118/691 |
| 6,241,886 B1 | 6/2001 | Kitagawa et al. | |
| 6,346,192 B2 | 2/2002 | Buhr et al. | |
| 6,463,656 B1 * | 10/2002 | Debesis | B41J 2/16 29/825 |
| 2002/0106643 A1 | 8/2002 | Kulseth et al. | |
| 2002/0168839 A1 * | 11/2002 | Yanagi et al. | 438/551 |
| 2003/0104359 A1 | 6/2003 | Cuthbertson et al. | |
| 2004/0182788 A1 | 9/2004 | Dorian et al. | |
| 2005/0048667 A1 | 3/2005 | Ellman et al. | |
| 2005/0074406 A1 | 4/2005 | Couvillon et al. | |
| 2005/0263452 A1 * | 12/2005 | Jacobson | 210/484 |
| 2006/0124865 A1 | 6/2006 | Wolfe et al. | |
| 2006/0228873 A1 | 10/2006 | Liu et al. | |
| 2006/0228897 A1 | 10/2006 | Timans | |
| 2007/0114207 A1 | 5/2007 | Hoffbauer et al. | |
| 2008/0088059 A1 | 4/2008 | Tang et al. | |
| 2009/0202813 A1 | 8/2009 | Itami | |
| 2009/0232336 A1 * | 9/2009 | Pahl | 381/175 |
| 2009/0258318 A1 * | 10/2009 | Chan | 430/312 |
| 2009/0297982 A1 * | 12/2009 | Saitou | G03F 7/031 430/286.1 |
| 2010/0003623 A1 * | 1/2010 | Liu | 430/326 |
| 2010/0038303 A1 | 2/2010 | Cai et al. | |
| 2010/0084747 A1 * | 4/2010 | Chen | H01L 21/6835 257/621 |
| 2010/0255479 A1 * | 10/2010 | Mikolajczyk et al. | 435/6 |
| 2012/0037591 A1 * | 2/2012 | Tringe et al. | 216/2 |
| 2012/0168940 A1 * | 7/2012 | Bieck | 257/737 |

* cited by examiner (A)

(B)

(A)

(B)

FABRICATION OF MICROFILTERS AND NANOFILTERS AND THEIR APPLICATIONS

This application claims benefit under 35 U.S.C. § 119 from U.S. Provisional Application No. 61/430,818, filed on Jan. 7, 2011, the entire content of which is incorporated herein by reference.

The present invention relates to U.S. Provisional Patent Application Ser. No. 61/330,819, filed May 3, 2010 and U.S. Provisional Patent Application Ser. No. 61/377,797, filed Aug. 27, 2010 the entire contents of which are incorporated herein by reference.

FIELD OF THE INVENTION

The invention relates to method to fabricate high-aspect-ratio precision nanopores and nanopillars in photo sensitive polymer films over large area by optical interference lithography using ultra-violet radiation. Free standing nanopores in polymer films with aspect ratio over 30 have been demonstrated in films greater than 10 micron thick. Interference lithography provides the same periodic pattern over the large area and through the entire film thickness.

The invention relates to method to fabricate precision micropores in polymer films by ultra-violet and x-ray lithography methods that provide (1) high volume manufacturing capability and (2) low cost production for a wide variety of polymers and film thicknesses. The invention also describes the use of the precision microfilters for medical applications, such as capture of circulating tumor cells in peripheral blood of cancer patients and primitive fetal nucleated red blood cells in peripheral blood of pregnant women. Other applications include collection of stromal cells, mesenchymal cells, endothelial cells, epithelial cells, stem cells, non-hematopoietic cells, and the like from a blood sample, and tumor or pathogenic cells from urine.

The present invention provides methods and compositions for isolating and detecting rare cells from a biological sample containing other types of cells. In particular, the present invention includes a procedure that uses a microfabricated filters for filtering fluid samples, from which the enriched cells can be used in downstream processes, such as identification, characterization, growth in culture, or used in other ways.

The final enriched target cells can be subjected to a variety of analyses and manipulations, such as staining, immunofluorescence, cell counting, PCR, fluorescence in-situ hybridization (FISH), immunohistochemistry, flow cytometry, immunocytochemistry, image analysis, enzymatic assays, gene expression profiling analysis, efficacy tests of therapeutics, culturing of enriched cells, and therapeutic use of enriched rare cells. In addition, the depleted plasma protein and white blood cells can be optionally recovered and subjected to other analysis, such as inflammation studies, gene expression profiling, etc.

The microfabrication methods described are also applicable to fabrication of any free standing patterned polymeric films.

The invention describes the use of microfilters, using PerMX™ 3000 series, SUEX or other similar photoresist dry film materials, to enrich circulating tumor cells from whole blood or PBMCs.

DESCRIPTION OF RELATED ART

Optical interference lithography (IL) has been successfully applied to manufacture periodic structures. Although this technique offers the advantage of submicron resolution over large sample areas and through the entire resist thickness, most papers on this subject report aspect ratios below 2, which results in thin, fragile samples requiring structural support often provided by silicon frames.

Commercial nanopore polymer filters produced by track etch have thickness ranging from 6 to 25 microns. The pores are located randomly and they often overlap resulting in large holes. Often, many layers of the filters have to be used at the same time to avoid losing the analyte to be captured. The track etch pores are also not straight. For some applications, it is not a desirable feature.

Commercial filters with high pore density can also be obtained by aluminum anodizing. The thicknesses of these filters are typically 60 µm. They have wide distribution of pore sizes and are not bio-compatible.

Use of microfilters to enrich circulating tumor cells was first published by Giovanna Vona et al. in 2000. [Giovanna Vona, Abdelmajid Sabile, Malek Louha, Veronique Sitruk, Serge Romana, Karin Schütze, Frédérique Capron, Dominique Franco, Mario Pazzagli, Michel Vekemans, Bernard Lacour, Christian Bréchot and Patrizia Paterlini-Bréchot. 2000. Isolation by Size of Epithelial Tumor Cells—A New Method for the Immunomorphological and Molecular Characterization of Circulating Tumor Cells, *American Journal of Pathology.* 2000; 156:57-63.] The authors used track etched filters, where the pore distribution is random and porosity is low.

More recently, Richard Cote of the University of Miami demonstrated CTC recovery using microfilters fabricated by Yu-Chong Tai of California Institute of Technology. Tai's laboratory produced micro pores in parylene film by UV Lithography and reactive ion etching (RIE). [Siyang Zheng, Henry Lin, Jing-Quan Liu, Marija Balic, Ram Datar, Richard J. Cote, Yu-Chong Tai. 2007. Membrane microfilter device for selective capture, electrolysis and genomic analysis of human circulating tumor cells, J. Chromatography A. 1162, 154-161. Yu-Chong Tai, Siyang Zheng, Henry Lin, Ram Datar and Richard Cote, "Uses of Parylene Membrane filters, WO 2006/116327 A1, published on Nov. 2, 2006. Yu-Chong Tai, Siyang Zheng, Henry Lin, Ram Datar and Richard Cote, "Membrane Filter for Capturing Circulating Tumor Cells", US Patent Application Publication, US 2006/0254972, Pub. Date: Nov. 16, 2006. Yu-Chong Tai, Siyang Zheng, Henry Lin, Ram Datar and Richard Cote, "Use of Parylene Membrane Filters", US Patent Application Publication, US 2007/0025883 A1, Pub. Date: Feb. 1, 2007. Siyang Zheng, Richard Cote, Henry Lin, Bo Lu and Yu-Chong Tai, "Method and Apparatus for Microfiltration to Perform Cell Separation", US Patent Application Publication, US 2009/0188864 A1, Pub. Date: Jul. 30, 2009.] Each filter is a 1×1 cm square with pores occupying a 6×6 mm area. The optimal pore dimension proved to be 7-8 microns in diameter. Within the 6×6 mm area, 40,000 pores are evenly distributed. There was virtually no clogging. [Martin Fleisher, Circulating Tumor Cells—A New Opportunity for Therapeutic Management of Cancer Patients, Clinical Laboratory News, November 2008, Vol. 34, No. 11, 10-12].

The UV lithography/Reactive ion etching (RIE) fabrication process used by Tai is fairly standard, but requires many steps and manual efforts and time.

A parylene microfilter, can be fabricated by conventional technology consisting of the following steps: (i) deposition of parylene on substrate, (ii) deposit metal that serves as a mask material for RIE, (iii) spin coat photoresist, (iv) expose photoresist through optical mask by UV lithography, (v) develop photoresist, (vi) remove metal from developed areas, (vii) perform RIE to form holes in parylene, (viii) remove photoresist, (ix) remove metal from the entire area, (x) remove parylene microfilters from substrate. The details of the process may vary.

X-rays can be used to pattern photoresists such as PMMA and SU-8 to make microfilters in those materials attached to a substrate.

X-rays have also been used successfully to etch mylar glued to a substrate. [Deis G A, Gavryushkina N I, Prokopenko V S, Artamonova L D, Gentcelev A N, Skrinsky A N, Sinyukov M P, Kulipanov G N, Pindyurin V P, Li C B, Mezentseva L A, Redin O A, Makarov O A, Gashtold V N (1995) Microporous membrane and method of it fabrication, Russian Federation Patent 2047334; Kulipanov G N, Makarov O A, Mezentseva L A, Mishnev S I, Naz'mov V P, Pindyurin V P, Redin O A, Skrinsky A N, Artamonova L D, Cherkov G A, Deis G A, Gashtold V N, Prokopenko V S, Chesnokov V V, Reznikova E F (1995) Fabrication and preliminary testing of regular microporous membranes manufactured by deep X-ray lithography at the VEPP-3 storage ring. Nuclear Instruments and Methods in Physics Research A 359: 404-408.]

Parylene microfilters with precise pore dimensions have been applied to isolate circulating tumor cells (CTCs) in peripheral blood. The use of parylene microfilters with 8 μm diameter pores found CTCs in 92.9% of patient samples, as compared to only 45.6% of samples using immunomagnetic beads, in a clinical trial at Memorial Sloan-Kettering, which used both devices on blood samples taken from patients with metastatic prostate cancer [Zosia Chustecka, AACR 2009: Measuring Circulating Tumor Cells Is Clinically Useful, New Technique Promises to Be Faster, http://www.medscape.com/viewarticle/701687] The filtration process was rapid, taking only 90 seconds to process a 7.5 ml sample of blood.

SUMMARY OF THE INVENTION

The invention describes methods to pattern and etch predetermined pore sizes, distributions and shapes in one or more layers of polymer films simultaneously using ultraviolet (UV) lithography or x-rays lithography. The process can also be automated, where one or more layers of the films are supplied in rolls. For each exposure, the films advance by the appropriate amount. During the exposure, the films are held securely in place. After the exposure, the film advances and process repeats. After exposure, the exposed films are developed to form the pores.

The microfabrication methods described are also applicable to fabrication of any free standing patterned polymeric films.

Exemplary embodiments of the present invention describe applications and methodologies utilizing precision microfilters. There is a wide variety of applications for microfilters including medical purposes, water filtration, beer and wine filtration, pathogen detection, etc. Exemplary polymer materials that are suitable for microfiltration are PerMX™ 3000 series, SUEX, and SU-8.

An exemplary embodiment of this invention describes using microfilters circulating tumor cells (CTCs) from peripheral blood in cancer patients.

Another exemplary embodiment of this invention describes using microfilters made from one or more of a variety of polymer materials, applied to enrich primitive fetal nucleated red blood cells in peripheral blood of pregnant women, Other applications include enriching stromal cells, mesenchymal cells, endothelial cells, epithelial cells, stem cells, non-hematopoietic cells, etc., from blood samples and tumor or pathogenic cells in urine.

The present invention provides methods and compositions for isolating and detecting rare cells from a biological sample containing other matter and other types of cells. In particular, the present invention includes a step that uses microfabricated filters for filtering fluid samples and the enriched cells can be used in downstream processes, such as identification, characterization, growth in culture, or used in other ways.

The final enriched target cells can be subjected to a variety of analyses and manipulations, such as staining, immunofluorescence, cell counting, PCR, fluorescence in-situ hybridization (FISH), immunohistochemistry, flow cytometry, immunocytochemistry, image analysis, enzymatic assays, gene expression profiling analysis, efficacy tests of therapeutics, culturing of enriched cells, and therapeutic use of enriched rare cells. In addition, the depleted plasma protein and white blood cells can be optionally recovered and subjected to other analysis, such as inflammation studies, gene expression profiling, etc.

Another exemplary embodiment of the present invention provides methods and devices for removing CTCs from circulation using microfilters. An exemplary application of this embodiment is for therapy.

Another aspect of the invention describes methods to pattern micropores and nanopores in thick polymer films using optical interference lithography.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 1A shows a side view of a negative resist dry film laminated to a removable substrate. FIG. 1B shows a side view of an exposure by UV lithography of a negative resist dry film laminated to a removable substrate. FIG. 1C shows a side view of the negative resist dry film on removable substrate during post bake. FIG. 1D shows a side view of the negative resist film after development while still attached to the substrate. FIG. 1E shows a side view of the microfilters after releasing from the substrate.

FIG. 2A shows a side view of a negative resist dry film laminated to copper foil. FIG. 2B shows a side view of the exposure of a negative resist dry film by UV lithography. FIG. 2C shows a side view of placing the exposed negative resist film laminated to copper foil for post bake. FIG. 2D shows the negative resist film after development while still attached to copper.

FIG. 3A shows a side view of a negative resist dry film laminated to KAPTON and a thin foil. FIG. 3B shows a side view of the exposure of a negative resist dry films by UV lithography. FIG. 3C shows placing the exposed negative resist films on KAPTON for post bake. FIG. 3D shows the negative resist films after development while still attached to KAPTON.

FIG. 4A shows a side view of a positive resist dry film laminated to a removable substrate. FIG. 4B shows a side view of an exposure by UV lithography of a positive resist dry film laminated to a removable substrate. FIG. 4C shows a side view of the positive resist film after development while still attached to the substrate. FIG. 1E shows a side view of the microfilters after releasing from the substrate.

FIG. 5A shows the negative resist film mounted on rolls and located beneath an exposure mask and above a support. After exposure, the film is advanced. FIG. 5B shows that each UV exposure will expose of the film.

FIG. 6A shows the top view of an array of round pores spaced equal distance from each other. FIG. 6B shows the top view of round pores arranged in a different array format. FIG. 6C shows the top view of pores with shape other than round. The pores can be arranged in groups. FIG. 2D shows a microfilter with more than one pore dimension.

FIG. 7A shows the side view of a pore where the thickness of the film is approximately the size of the pore. FIG. 7B shows the side view of a pore where the film thickness is larger than the pore diameter. FIG. 7C shows the side view of the microfilter film where the pores can have more than one dimension. FIG. 7D shows that the pores can have an opening on one surface that is larger than the opening on the other surface.

FIG. 8A shows a side view of the exposure by x-ray lithography of a stack of negative resist films. FIG. 8B shows the placing of the exposed negative resist films on a post bake substrate. FIG. 8C shows the negative resist films after development while still attached to the post bake substrate. FIG. 8D shows the negative resist films or microfilters after releasing from the post bake substrate.

FIG. 9A shows a side view of the exposure by x-ray lithography of a stack of negative resist films, each of which is laminated to a removable post bake substrate, where the substrate material is sufficiently transparent to x-rays. FIG. 9B shows the negative resist films on removable post bake substrate during post bake. FIG. 9C shows the negative resist films after development while still attached to the post bake substrate. FIG. 9D shows negative resist films or microfilters after release from the post bake substrate.

FIG. 10A shows a side view of the negative resist mounted on rolls. Several rolls of film can be mounted at the same time. After exposure, the film is advanced. FIG. 10B shows that each x-ray exposure will expose all layers of the film.

FIG. 12A shows a side view of a stack of negative resist films laminated to a removable post bake substrate before application of electrostatic chuck to hold the negative resist films in place. FIG. 12B show side view of the exposure of a stack of negative resist films during x-ray exposure when the electrostatic chuck is used to hold the films in place.

FIG. 13A shows a side view of the exposure of a stack of positive resist films by x-ray lithography. FIG. 13B shows the positive resist films separated before entering development. FIG. 13C shows positive resist films or microfilters after development.

FIG. 14A shows the positive resist films mounted on rolls. Several rolls of film can be mounted at the same time. After exposure, the film is advanced. FIG. 14B shows that each x-ray exposure will expose all layers of the film.

FIG. 16A shows side view of a stack of positive resist films before application of electrostatic chuck to fix the positive resist films. FIG. 16B show side view of exposure of a stack of positive resist films during x-ray exposure when the electrostatic chuck is used to fix the films.

FIGS. 18A-18L describe the steps to fabricate micropores using dry film in two layers. FIGS. 18A-18E describe the steps to fabricate strips of trenches on the first layer. The fabrication steps for FIGS. 18A-18D are the same as FIGS. 2A-2D. FIG. 18D shows the cross-sectional side view after development for the first layer from one direction and FIG. 18E shows the cross-sectional side-view rotated by 90°. FIGS. 18F-18L describe the steps to fabricate strips of trenches on the second layer. FIG. 18F describes lamination of a second negative resist dry film on the developed first layer of negative resist dry film. The fabrication steps for 18G-18J are the same as steps 18B-18D. FIG. 18I shows the cross-sectional side view of the two layers after development from one direction and FIG. 18J show the cross-sectional side-view rotated by 90°. FIG. 18K shows the cross-sectional side view of the two layers microfilter after removing substrate from one direction and FIG. 18L show the cross-sectional side-view rotated by 90°.

FIGS. 19A-19C show the top view of the microfilter fabrication process. FIG. 19A shows the top view of the pattern of trenches in the dry film on copper after step shown in FIG. 18E. FIG. 19B shows the top view of trenches in the dry film on copper after step shown in FIG. 18J. On each layer the pattern are strips of trenches. The strips of trenches on one layer are perpendicular to strips of trenches on the other layer. The pore is at the intersection of the strips. FIG. 19C shows the top view of the free standing filter after removing copper substrate after step shown in FIG. 18K.

FIGS. 20A-20G describe fabrication steps to fabricate micropores using dry film in three layers. FIG. 20A describe laminating a third negative photoresist dry film to the completed structure with already two negative photoresist dry film layers, i.e., following step FIG. 20J. The fabrication steps for FIGS. 20B-20D are the same as FIGS. 20B-20D. FIG. 20D shows the cross-sectional side view after development from one direction and FIG. 20E show the cross-sectional side-view rotated by 90°. FIG. 20F shows the cross-sectional side view of the final microfilter after removal of substrate from one direction and FIG. 20G show the cross-sectional side-view the rotated by 90°.

FIG. 21 shows the top view of the microfilter after removal of copper. In this drawing the pores on top and bottom are not aligned, but the pores are interconnected.

FIG. 22 shows the method to expose the photoresist by interference lithography using liquid resist as a starting material.

FIG. 23 shows the method to expose the photoresist by interference lithography using a premade dry resist film.

FIG. 24 shows SEM of nanofilter showing the pores obtained at the front side.

FIG. 25 is a cross-sectional SEM image of a processed resist showing pore depth to 2.7 micron.

FIG. 26 shows ores on the back-side of the developed freestanding 9 micron SU 8 membrane (the cross section shows that the film is fully developed).

DETAILED DESCRIPTION OF EXEMPLARY EMBODIMENTS

Figure 1:
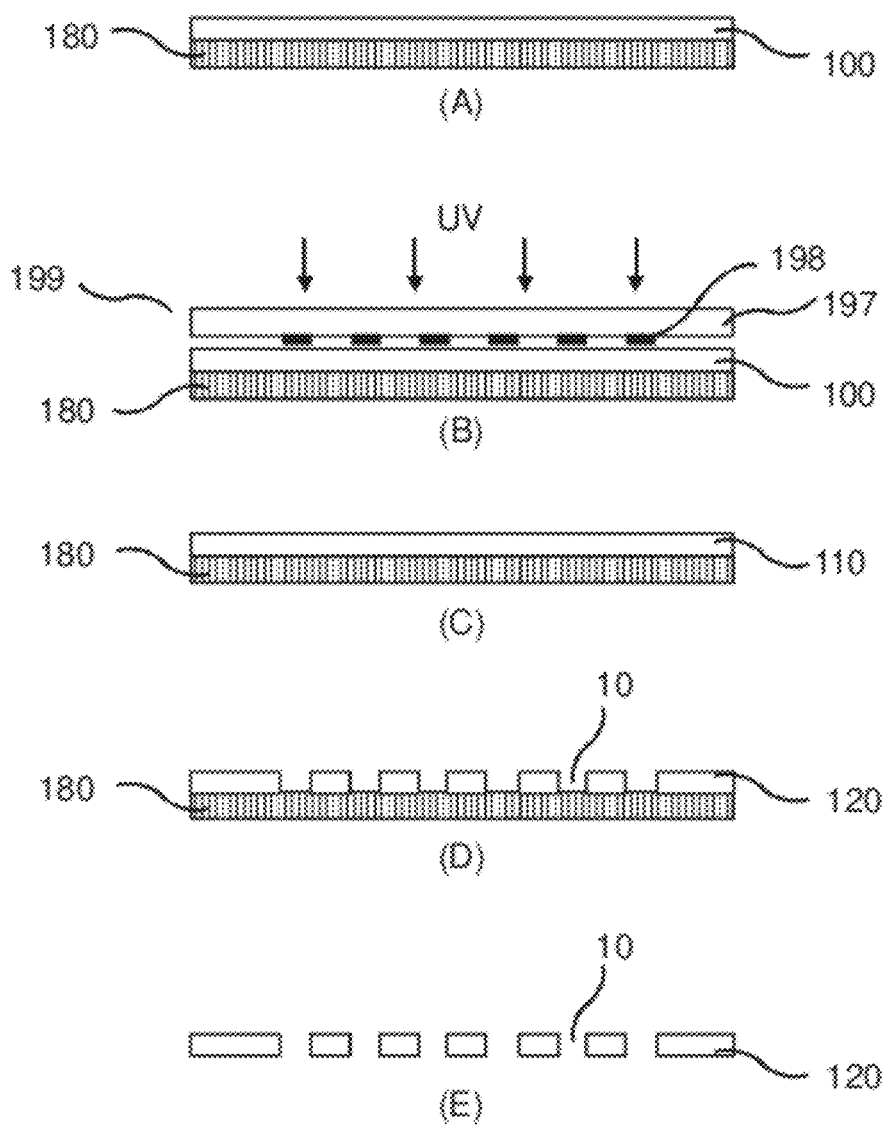
FIGS. 1A-1E.

Referring now to the drawings, wherein like reference numerals designate identical or corresponding parts throughout the several views, embodiments of the present invention are shown in schematic detail.

The matters defined in the description such as a detailed construction and elements are nothing but the ones provided to assist in a comprehensive understanding of the invention. Accordingly, those of ordinary skill in the art will recognize that various changes and modifications of the embodiments described herein can be made without departing from the scope and spirit of the invention. Also, well-known functions or constructions are omitted for clarity and conciseness. Exemplary embodiments of the present invention are described below in the context of certain exemplary applications. Such exemplary implementations are not intended to limit the scope of the present invention, which is defined in the appended claims.

We disclose methods of fabricating free standing precision micropores that is not based on track etching of polymers or use of solid parylene films.

The proposed precision microfilters can be made of variety of polymers, such as polycarbonates, polyesters, in particular polyethylene terephthalate (PET) (Mylar™), SU-8, KMPR, PerMX™, SUEX, polymethylmethacrylate (PMMA), polymethylglutarimide (PMGI), etc.

Many of these materials can be obtained as dry films in a variety of thickness from less than 10 µm to more than 100 µm.

We present method of fabrication based on UV lithography and on x-ray lithography without using reactive ion etching (RIE).

UV Lithography of Microfilters

Negative resists refers to polymers that becomes polymerized when exposed to UV or x-rays, while positive resist refers to polymers in that the polymeric bonds are broken by UV or x-rays. For resist layers that are greater than a few microns in thickness, negative resists are generally much more sensitive than positive resists.

Examples of commercially available negative resists that are in liquid form are SU-8 and KMPR from MicroChem, but not limit to them. Commercially available negative resist dry films are PerMX™ series (DuPont), SUEX (DJ DevCorp), and others. PerMX™ 3000 series is manufactured in roll by DuPont. The commercially available thicknesses for PerMX™ are 10 µm, 14 µm, 25 µm, and 50 µm. Other thickness can also be obtained on custom order bases.

Positive resist dry films are also commercially available, for example PMMA.

1. Fabricate Microfilters from a Single Layer of Negative Resist Using UV Lithography There are a number of methods to fabricate microfilters using negative resists. An exemplary implementation illustrating a general concept is described first in the context of Example 1.A. Variations of the concept include, but are not limited to, other exemplary implementations which are described in the context of further Examples that follow.

Example 1.A. Microfilter Fabrication Using Negative Resist Dry Films Laminated on Removable Substrate by UV Exposure The fabrication steps are:
a. Laminate negative resist dry film 100 on removable substrate 180, as shown in FIG. 1A.
b. Expose the negative resist dry film 100 laminated on removable substrate 180 to UV light though the microfilter optical mask 199 with pattern 198 formed by thin film of chromium, FIG. 1B.
c. Post bake the exposed dry film 110 on removable substrate, FIG. 1C.
a. Develop the exposed dry film to form microfilter 120 with pores 10 on removable substrate 180, FIG. 1D. The parts of the negative resists that are not exposed to the UV are dissolved by developer.
d. Hard bake developed dry film (optional).
e. Remove substrate and to obtain free standing microfilter 120 with pores 10, FIG. 1E.

Figure 2:
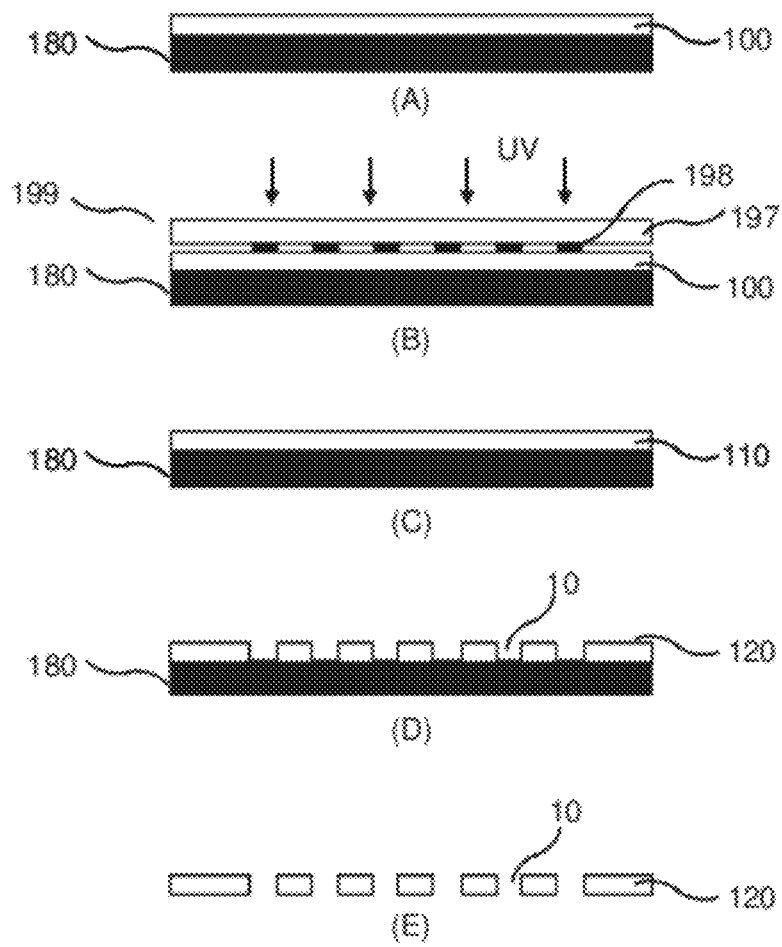
FIGS. 2A-D.
FIG. 2E shows negative resist microfilters after removing copper foil.

Example 1.B. Microfilter Fabrication Using Negative Resist Dry Films Laminated on Copper Foil Substrate Using UV Exposure The fabrication steps are:
f. Obtain or laminate negative resist dry film 100 on thin copper foil 20, as shown in FIG. 2A.
g. Expose the negative resist dry film 100 laminated on copper foil 180 to UV though the microfilter optical mask 199 with pattern 198 formed by thin film of chromium, FIG. 2B.
h. Post bake the exposed dry film 110 on copper foil, FIG. 2C.
i. Develop the negative resist to form microfilter 120 with pores 10 on copper substrate 180, FIG. 2D.
j. Hard bake (optional).
k. Etch away copper and to obtain free standing microfilter 120 with pores 10, FIG. 2F.

Example 1.C. Microfilter Fabrication Using Negative Resist Dry Films on Kapton Release Layer The fabrication steps using KAPTON as a release layer are:
a. Laminate negative resist dry film 100 on KAPTON film 181. Along the edge(s) or other pre-specified location, a separation assistant material 182 is placed between the negative resist dry film and KAPTON as a separator, as shown in FIG. 3A. The separation assistant material 182 can be KAPTON, or other materials that can be laminated to the dry film and can withstand the hard bake temperature.
b. Expose the film to UV though the microfilter optical mask 199 with pattern 198 formed by thin film of chromium, FIG. 3B.
c. Post bake the exposed dry film 110 on KAPTON 181, FIG. 3C.
d. Develop the negative resist to form microfilter 120 with pores 10 on KAPTON 181, FIG. 3D.
e. Hard bake (optional).
f. Using the edge 182 where the negative resist film is not attached to KAPTON, peel the negative resist film from KAPTON to obtain free standing microfilters, FIG. 3E
g. Remove the separation assistant polymer 182 to obtain free standing microfilter 120 with pores 10, FIG. 3F.

Example 1.D: Microfilter Fabrication Using Liquid Negative Resist and Copper Release Layer The fabrication steps using copper as a release layer are:
a. Coat substrate, for example silicon wafer, with thin layer of copper.
b. Spin coat negative resist, such as SU-8 on copper, followed by pre-bake.

c. Expose the film to UV light though the microfilter optical mask.
d. Post bake.
e. Develop the negative resist to form pores.
f. Etch away copper and release the microfilters.

Example 1.E. Microfilter Fabrication Using Liquid Negative Resist and Positive Resist Release Layer A combination of use of negative resist and positive resist (PMGI, LOR from MicroChem, S1800 series photoresists from Shipley) can also be used to obtain free standing microfilters. The steps are:
a. Spin coat positive resist (such as PMGI) on substrate, such as silicon wafer, and followed by prebake.
b. Expose PMGI to UV at the appropriate dose for the coating thickness.
c. Spin coat negative resist, such as SU-8 on the positive photoresist followed by prebake.
d. Expose the SU-8 resist to UV though the microfilter optical mask.
e. Post bake.
f. Develop the negative resist to form pores.
g. Develop PMGI to release the microfilters.
Other positive resists can also be used as release layer.

Example 1.F. Microfilter Fabrication Using Negative Resist Dry Films on Copper Release Layer on Silicon Wafer The fabrication steps using copper as a release layer are:
a. Coat substrate, for example silicon wafer, with thin layer of copper.
b. Laminate negative resist dry film on copper
c. Expose the film to UV though the microfilter optical mask.
d. Post bake.
e. Develop the negative resist to form pores.
f. Hard bake (optional).
g. Etch away copper and release the microfilters.

Example 1.G. Microfilter Fabrication Using Negative Resist Dry Film on Positive Resist Release Layer a. Spin coat positive resist (such as PMGI) on substrate, such as silicon wafer.
b. Expose PMGI to UV at the appropriate dose for the coating thickness.
c. Laminate negative resist dry film on the positive resist.
d. Expose the SU-8 resist to UV though the microfilter optical mask.
e. Post bake.
f. Develop the negative resist to form pores.
g. Develop the positive resist to release the microfilters.

Figure 4:
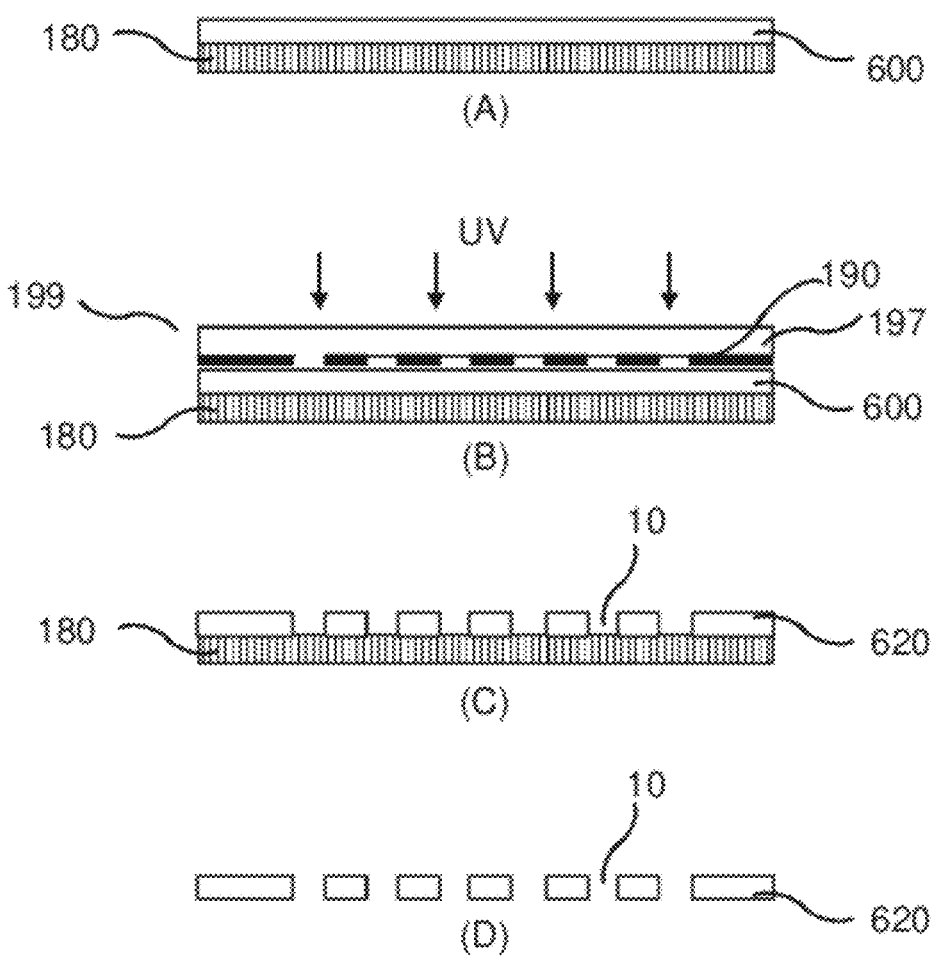
FIGS. 4A-4D.

Example 1.H. Microfilter Fabrication Using Positive Resist Dry Film on the Positive Resist Release Layer a. Laminate positive resist dry film 600 on removable substrate 180, as shown in FIG. 4A.
b. Expose the positive resist dry film 600 laminated on removable substrate 180 to UV light though the microfilter optical mask 199 with pattern 190 formed by thin film of chromium, FIG. 4B.
c. Develop the exposed dry film to form microfilter 620 with pores 10 on removable substrate 180, FIG. 4C. The parts of the positive resists that are exposed to the UV are dissolved by developer.
d. Remove substrate and to obtain free standing microfilter 620 with pores 10, FIG. 4D.

Example 1.I. Microfilter Fabrication Using Positive Resist Dry Film on Removable Substrate Such as Copper Foil a. Laminate positive resist dry film on the copper
b. Expose the positive resist dry film to UV though the microfilter optical mask. The parts of the positive resists that are exposed to the UV can be dissolved by developer.
b. Develop the positive resist to form pores.
c. Wet etch copper to release the microfilters.

Figure 3:
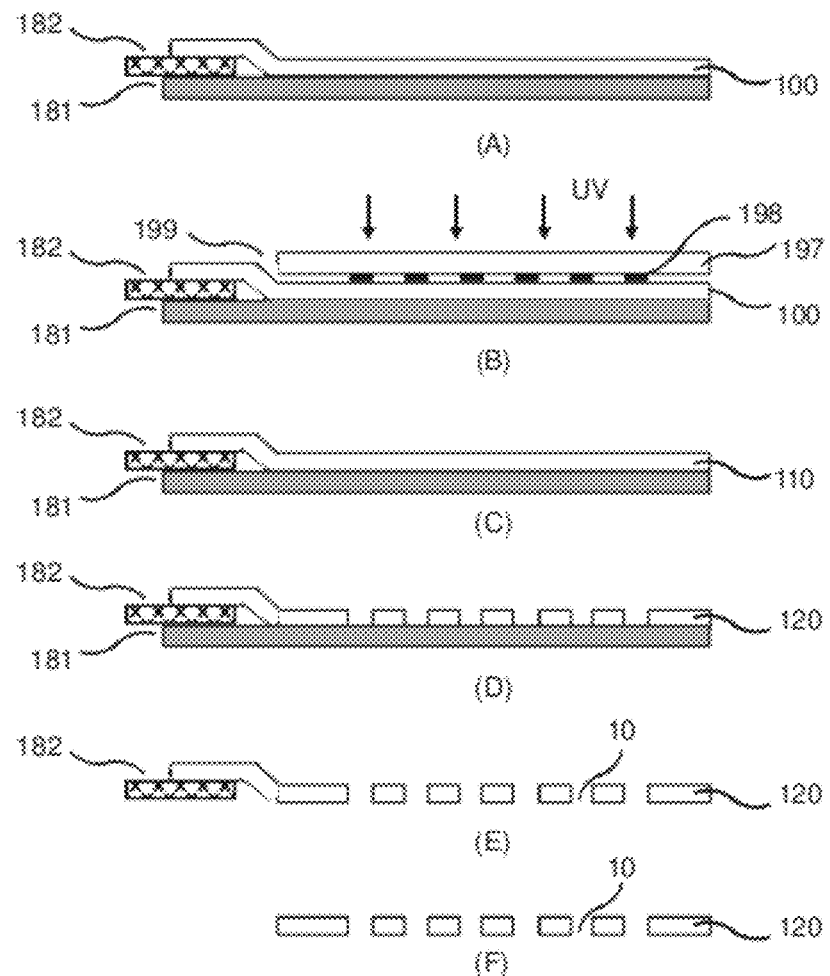
FIGS. 3A-D.
FIG. 3E shows negative resist microfilters after peeling off KAPTON.
FIG. 3F shows the finished microfilter.
Figure 5:
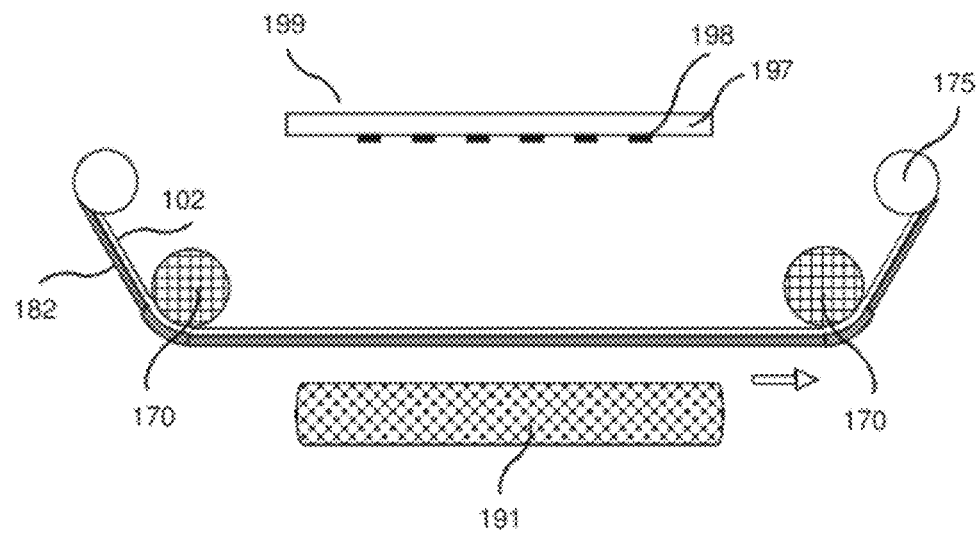
FIGS. 5A-B.
Figure 5:
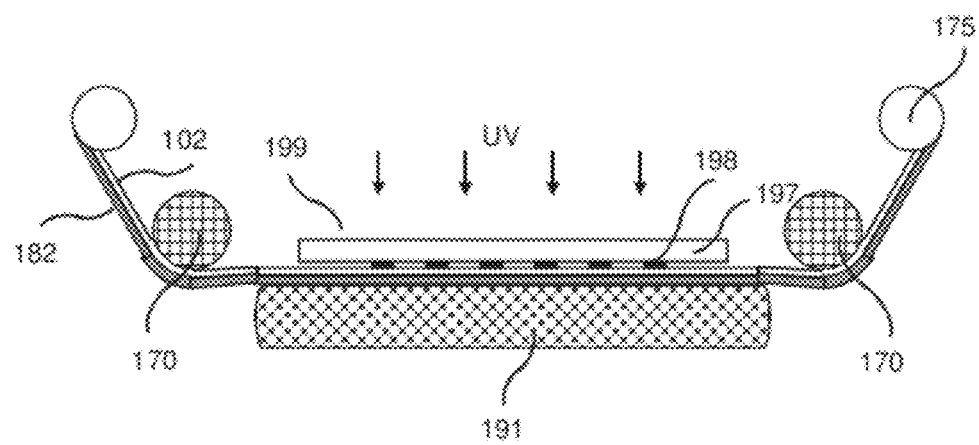

2. Fabricate Microfilters from a Roll of Negative Resists Dry Film Using UV Lithography Example 2.A: Microfilter Fabrication Using a Roll of Negative Resist Dry Film The negative resist dry film, such as PerMX™ 3000 series, is manufacture in roll form. To perform UV lithography of the resist in the role form as shown in FIG. 3 can simplify the fabrication. The method of implementation and steps of fabrication are described below.
a. Between each exposure, an unexposed portion of a roll of negative resist dry films is advanced as shown in FIG. 5A. The films 102 laminated on removable substrate 182 are connected by rolls 175. They are stretched by rollers 170. The rolls advance by the distance appropriate for the optical mask and exposure system as indicated by arrow. During film advance, the optical mask 199 and support 191 are moved away from the films.
b. During exposure, the stretched film 102 is pushed into the support 191 to provide additional tension and stability as shown in FIG. 5B. The UV exposure is performed after the optical mask 199 is placed on the films.
c. After the exposure, the roll of film advances through the oven for post bake.
d. Films are developed to obtain the pores.
e. The substrate 182 is removed to obtain free standing microfilters with pores. Individual microfilters are diced from the roll of dry film with pores.

Microfilter Variations

Figure 6:
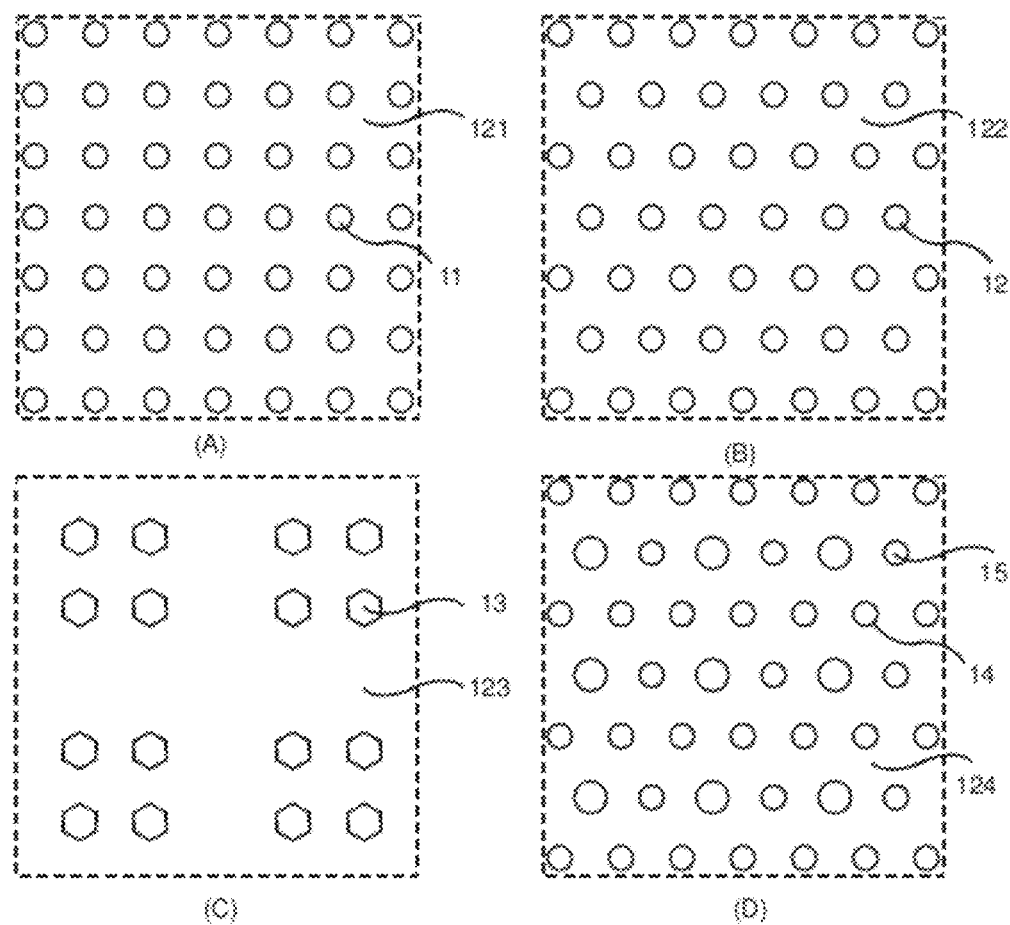
FIGS. 6A-D.

Since the applications of microfilters can vary, the pattern of the pores needs to be adjusted accordingly. The UV fabrication method described above can be used to fabricate circular uniform pores distributed as shown in FIGS. 6A, 6B or other distributions. The UV fabrication method can fabricate pores of different shape and grouping as shown in FIG. 6C, and other shapes. The UV fabrication methods can fabricate pores of different sizes as shown in FIG. 6D.

Figure 7:
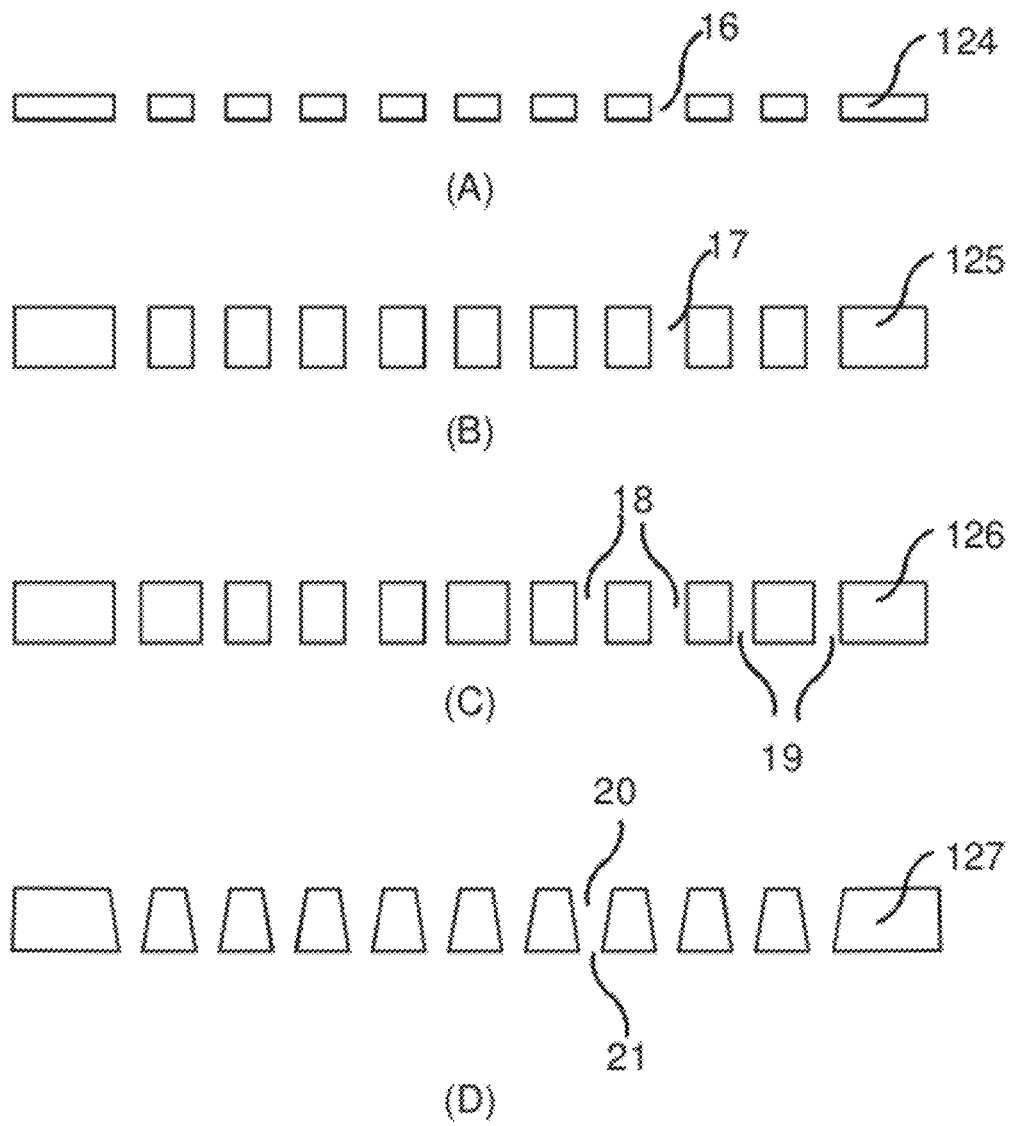
FIGS. 7A-D.

The cross sectional view of the microfilters for various thicknesses, FIGS. 7A and 7B. FIG. 7C shows a cross section where the pores has different sizes 18 and 19. Using negative resist, it is also possible to fabricate pores that have a smaller pore opening on top 20 compared with the opening of the pore on the bottom 21, in FIG. 7D. This can be accomplished by providing exposure dose that is higher than that is required to form uniform pore openings.

These are examples and method is applicable to other geometries and applications beside microfilters.

X-Ray Lithography of Microfilters

The penetration of x-rays is much deeper than UV. Unlike UV, it does not diverge within the thickness of less than 1 cm even for features much smaller than one micron. X-ray lithography is typically performed on a beamline of a synchrotron. X-ray lithography can be used for both negative and positive resists/polymers.

3. Fabricate Microfilters from a Stack of Negative Resists Using X-Rays Lithography

Figure 8:
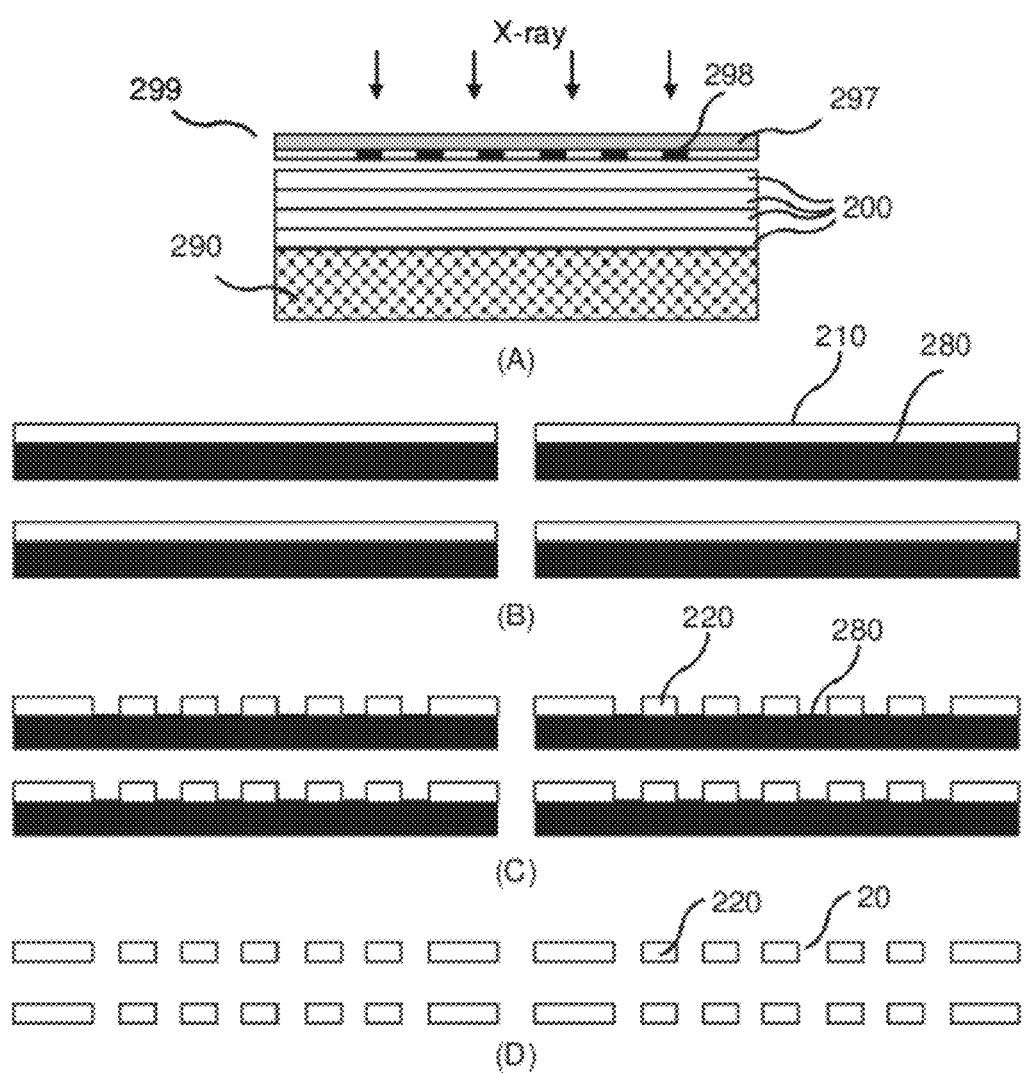
FIG. 8A-D.

Example 3.A: Using a Stack of Negative Resist Dry Films on Individual Wafers Using X-Ray Exposure The concept of microfabricating a stack of microfilters simultaneously by x-ray lithography using negative resist is illustrated in FIG. 8. The principle is very similar to that shown in FIG. 1 and described in Example 1.A. The steps of fabrication are described below.

a. A stack of negative resist dry films 200 are stretched and attached on a substrate 290 along the edge, by water soluble wax, glue, electrostatic chuck, clamp, and a variety of other methods b. Expose the stack of negative resist dry films to x-rays through an x-ray mask 299, which is typically made of gold 298 to block the x-rays on thin graphite sheet or silicon wafer 297. The parts of the negative resists that are not exposed to the x-ray are dissolved by developer.

c. The individual sheets of exposed negative resists 210 are to be separated, placed on post bake substrates 280 for post bake. During the post bake, the negative resist 210 will be attached to the post bake substrate 280. The post bake substrates needs to be able to stand the post bake temperature and can be dissolved chemically or by water.

d. The sample is developed 220 to form the pores, but still attached to the post bake substrate 280.

e. The post bake substrate is removed to obtain free standing microfilter 220 with pores 20 in the microfilter 220.

Figure 9:
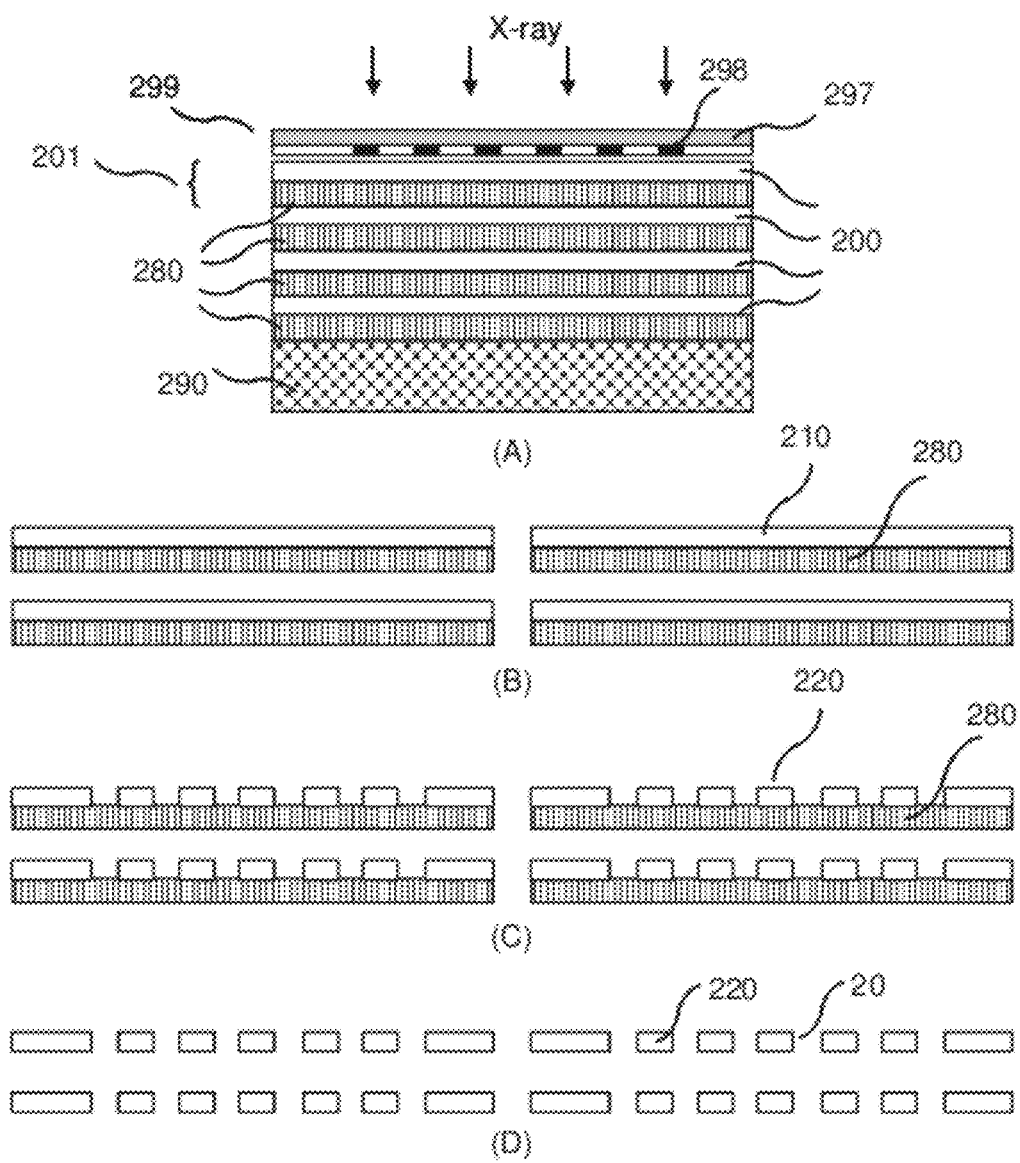
FIGS. 9A-D.

Example 3.B: Using a Stack of Negative Resist Dry Films Laminated to a Post Bake Substrate on Individual Wafers An alternative on the use of negative resist dry film is illustrated in FIG. 9. This eliminates the labor required to perform step c of Example 1.B. The steps of fabrication are described below.

a. The negative resist sheet 200 is laminated to a post bake substrate 180 with the properties of to be x-ray transparent, having melting point higher than post bake temperature and removable chemically.

b. A stack of negative resist sheet on post bake substrates 201 are stretched and attached on a substrate 290 along the edge, by water soluble wax, glue, clamp, and a variety of other methods.

c. The negative resist sheet laminated on post bake substrates 201 are separated for post bake.

d. The negative resist dry film laminated on post bake substrates are developed to obtain pores. The developed negative resist dry film 220 are still attached to the post bake substrates 280.

e. The post bake substrate is removed to obtain free standing microfilter 220 with pores 20 in the microfilter 220.

Figure 10:
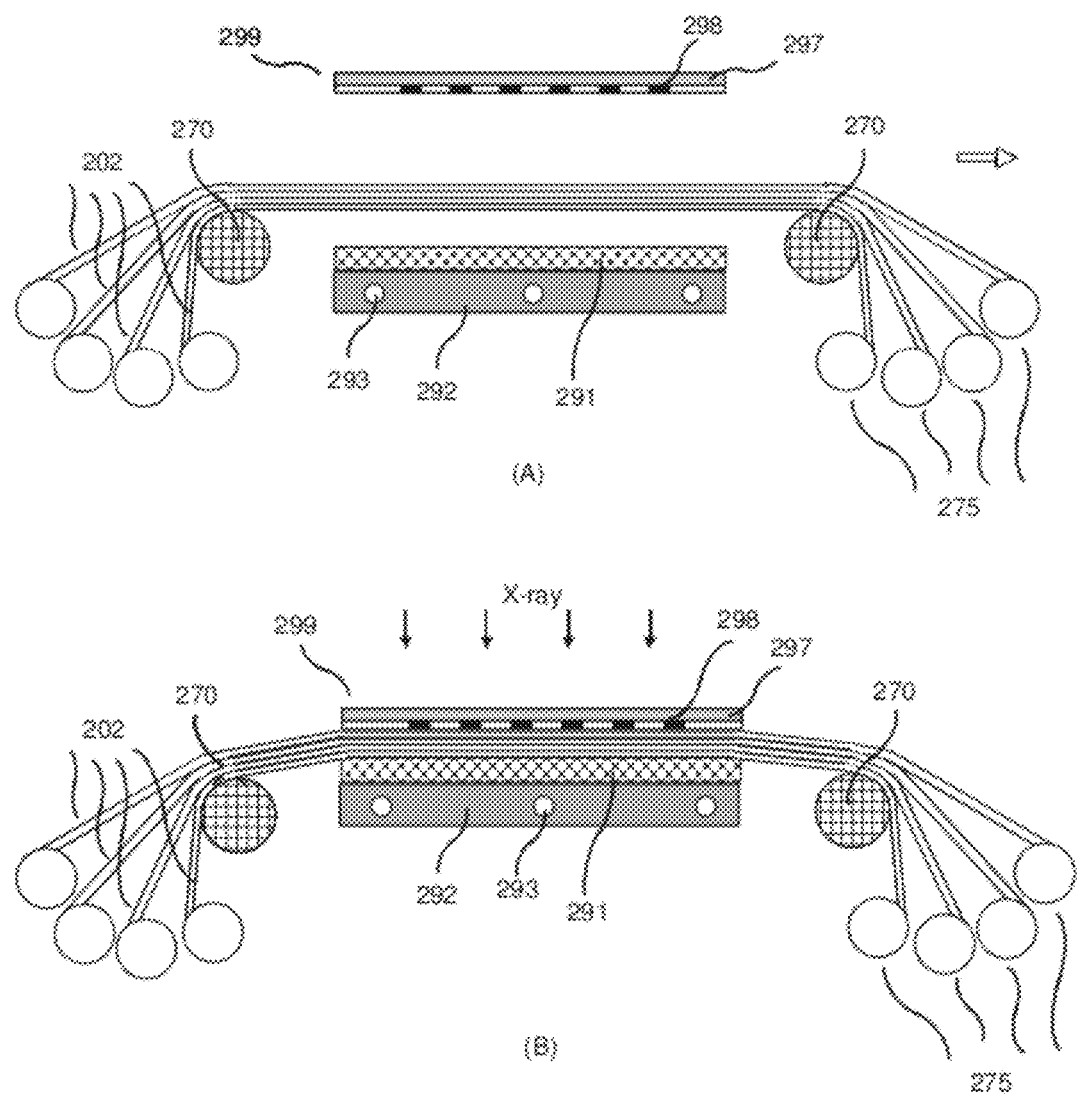
FIGS. 10A-B.

Example 3.C: Fabrication Microfilters in a Roll of Negative Resist Dry Film The negative resist dry film, such as PerMX™ series, is manufactured in a roll form. To perform x-ray lithography of the resist in the role form as shown in FIG. 10 can simplify the fabrication. The method of implementation and steps of fabrication are described below.

a. Between each exposure, one or more rolls of negative resist films are shown in FIG. 10A. The films 202 are connected by rolls 275. They are stretched by rollers 270. The rolls advance by the distance appropriate for the x-ray mask and exposure system as indicated by arrow. During film advance, the x-ray mask 299, support 291, water cooling frame 292 and duct 293 are moved away from the films.

b. During exposure, the stretched films 202 are pushed into the support 191 to provide additional tension and stability as shown in FIG. 10B. The x-ray exposure is performed after the x-ray mask 299 is place on the stack of stretched films.

c. After the exposure, the films are post baked on a post bake substrate d. Films developed.

e. The post bake substrate is removed to obtain free standing microfilters with pores.

Figure 11:
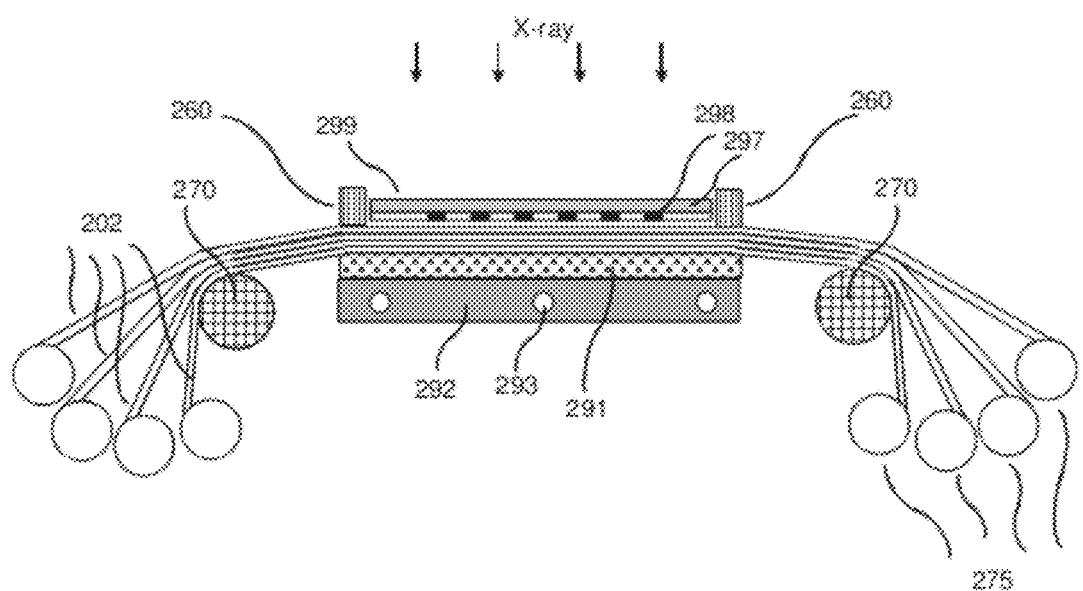
FIG. 11 shows that the films are pressed at the edges of the mask during x-ray exposure to prevent motion.
Figure 12:
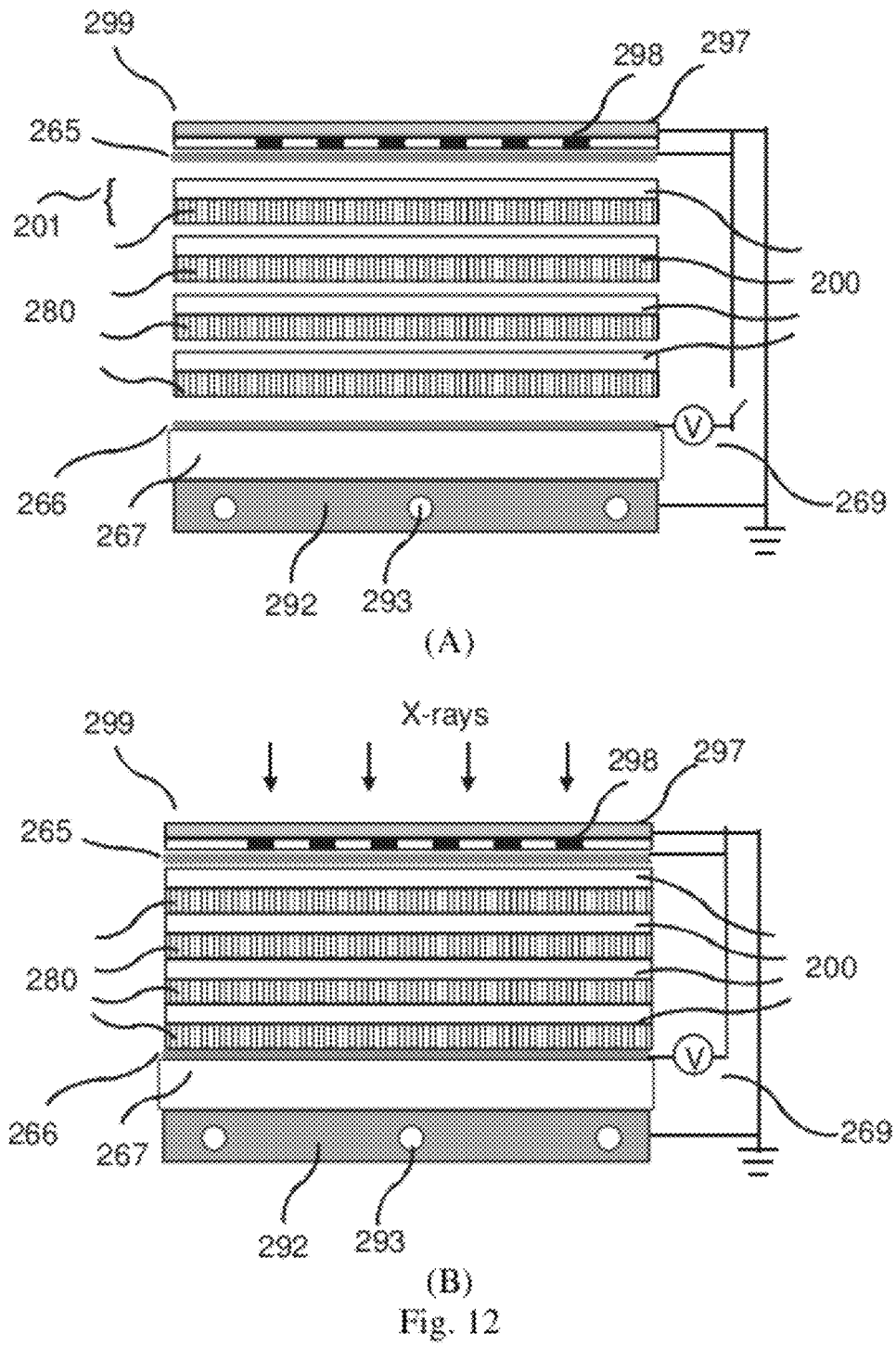
FIGS. 12A-B.

There are many potential variations. (i) The film can be just one roll or as many rolls as appropriate for fabrication of precision pore dimensions. (ii) The films can be laminated with post bake substrate. (iii) The films can be further held fixed by additional clamp or fixture 260 around the x-ray mask, as shown in FIG. 11. (iv) The stack is held secure by electrostatic force, as shown in FIG. 12.

Example 3.D: Fabrication Microfilters in a Roll of Negative Resist Dry Film and Applying Electrostatic Chuck to Fix the Films In FIG. 12, the concept of using electrostatic force to hold the films secure is shown, but the rollers are not shown. In FIG. 12A, the configuration of the system is shown between exposures. The one or more laminated negative resist film 200 laminated to post bake support film 280 to form films 201. A stack of films 201 are stretched. The substrate structure consist of a support 292, an insulator 267 and a conduction layer 266. A clear conducting film 265 is placed on top of the film. Voltage 269 is set to zero and the circuit is open.

FIG. 12B shows the configuration during exposure, where a voltage 169 is applied between the electrodes 265 and 266. This allows the films to be tightly fixed between the electrodes to avoid motion. The x-ray mask is place adjacent to the electrode 265 and exposure is performed.

If the films are not pre-laminated, finish fabrication following the steps c-e of Example 2.A. If the films are pre-laminated, finish fabrication following the steps c-e of Example 2.B.

4. Fabricate Microfilters from a Stack of Positive Resists Using X-Rays

Figure 13:
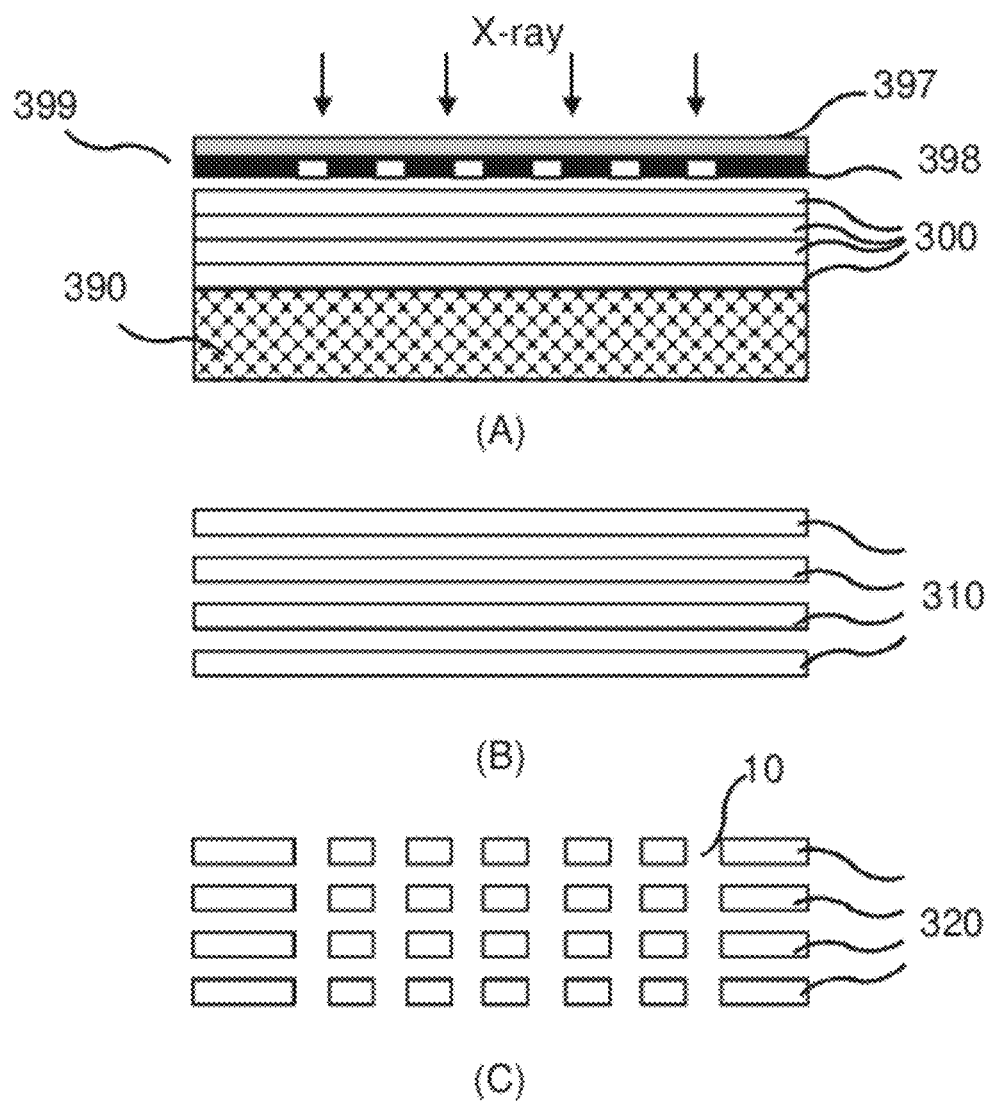
FIG. 13A-C.

Example 4.A: Using a Stack of Positive Resist Sheets on Individual Wafers Using X-Ray Exposure The concept of microfabricating a stack of microfilters simultaneously by x-ray lithography using positive resist is illustrated in FIG. 13. The steps of fabrication are described below.
- a. A stack of polymers sheets 300 that have the properties of positive resist are stretched and attached on a substrate 390 along the edge, by water soluble wax, glue, clamp, and a variety of other methods.
- b. Expose the stack of positive resist sheets to x-rays through an x-ray mask 399, which is typically made of gold absorber 398 on thin graphite sheet or silicon wafer 397. The parts of the polymer film that are exposed to the x-ray can be dissolved by developer.
- c. The individual sheets of exposed positive resists 310 to be placed in the developer
- d. The finished developed sample 320 with pores is shown in FIG. 13C

Example 4.B: Fabrication Microfilters from a Roll of Positive Resist Films

Figure 14:
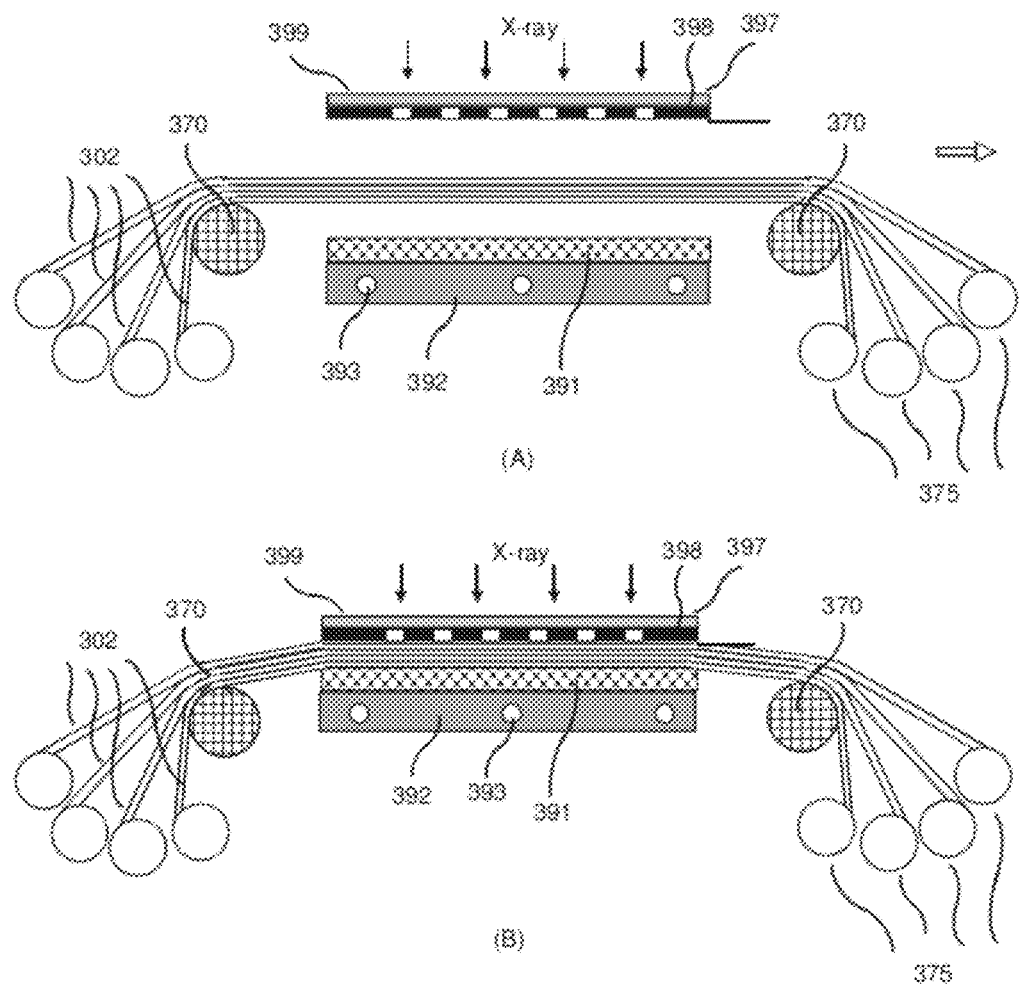
FIGS. 14A-B.

Most polymers belong to the category of positive resist films. Examples are polycarbonates, polyesters such as polyethylene terephthalate (PET) (Mylar™), etc. To perform x-ray lithography of the resist in the role form as shown in FIG. 14 can simplify the fabrication and allow high volume production. The method of implementation and steps of fabrication are described below.
- a. Between each exposure, one or more rolls of positive resist films are shown in FIG. 14A. The films 300 are connected by rolls 375. They are stretched by rollers 370. The rolls advance by the distance appropriate for the x-ray mask and exposure system as indicated by arrow. During film advance, the x-ray mask 399, support 391, water cooling frame 392 and duct 393 are moved away from the films.
- b. During exposure, the stretched films 300 are pushed into the support 391 to provide additional tension and stability as shown in FIG. 14B. The x-ray exposure is performed after the x-ray mask 299 is place on the stack of stretched films.
- c. Films are developed to obtain free standing microfilters with pores.

Figure 15:
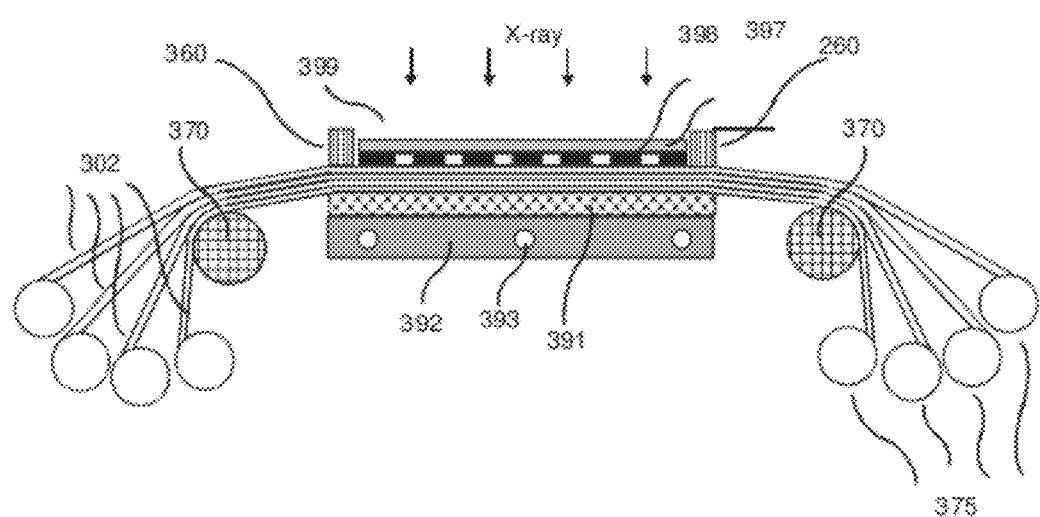
FIG. 15 shows that the films are pressed around the border of the positive resist films during x-ray exposure to prevent motion.
Figure 16:
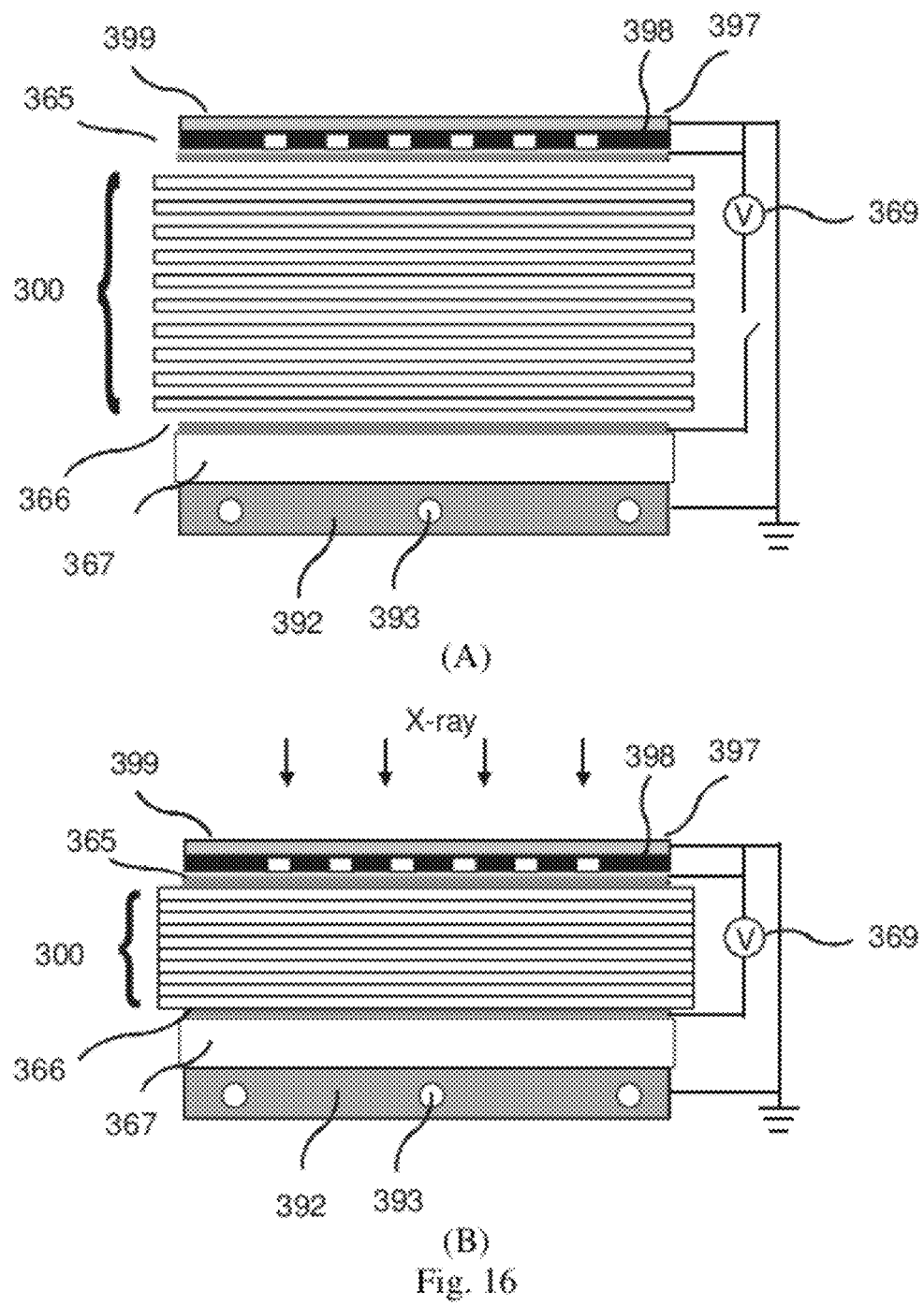
FIGS. 16A-B.

There are many potential variations. (i) The film can be just one roll or as many rolls as appropriate for fabrication of precision pore dimensions. (ii) The films can be further held fixed by additional clamp or fixture 360 around the x-ray mask, as shown in FIG. 15. (iv) The stack is held secure by electrostatic force, as shown in FIG. 16.

Example 4.D: Fabrication Microfilters in a Roll of Positive Resist Film and Applying Electrostatic Chuck to Fix the Films

- a. In FIG. 16, the concept of using electrostatic force to hold the films secure is shown, but the rollers are not shown. In FIG. 16A, the configuration of the system is shown between exposures. The one or more laminated positive resist film 300 laminated to post bake support film 380 to form films 301. A stack of films 301 are stretched. The substrate structure consist of a support 392, an insulator 367 and a conduction layer 366. A clear conducting film 365 is placed on top of the film. Voltage 369 is set to zero and the circuit is open.
- b. FIG. 16B shows the configuration during exposure, where a voltage 369 is applied between the electrodes 365 and 366. This allows the films to be tightly fixed between the electrodes to avoid motion. The x-ray mask is place adjacent to the electrode 365 and exposure is performed.
- c. Fabrication can be finished by developing the films.

The various microfabrication methods described above are also applicable to fabrication of any free standing patterned polymeric films.

Thin, smooth copper films are preferable as a substrate, because irregularities of the copper surface that is laminated to the negative resist dry films are transferred to the dry films after removal of copper.

Thin copper films are preferred to minimize the amount of time required for its removal.

Thin copper films are preferred because better contact between mask and resist film can be achieved.

5. Fabrication of Microfilters from Two or More Layers of Filter Material

The method of fabrication to be described in this section can be performed by either UV or x-ray lithography.

Figure 18:
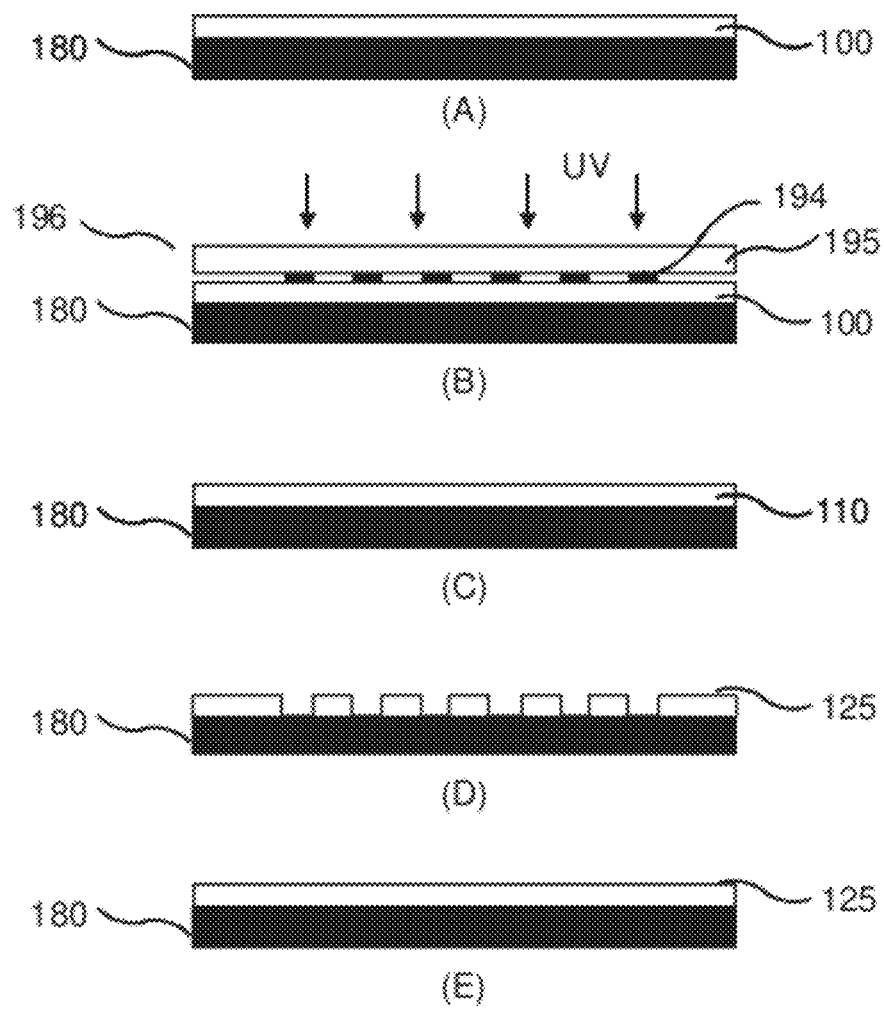
FIGS. 18A-18L.
Figure 18:
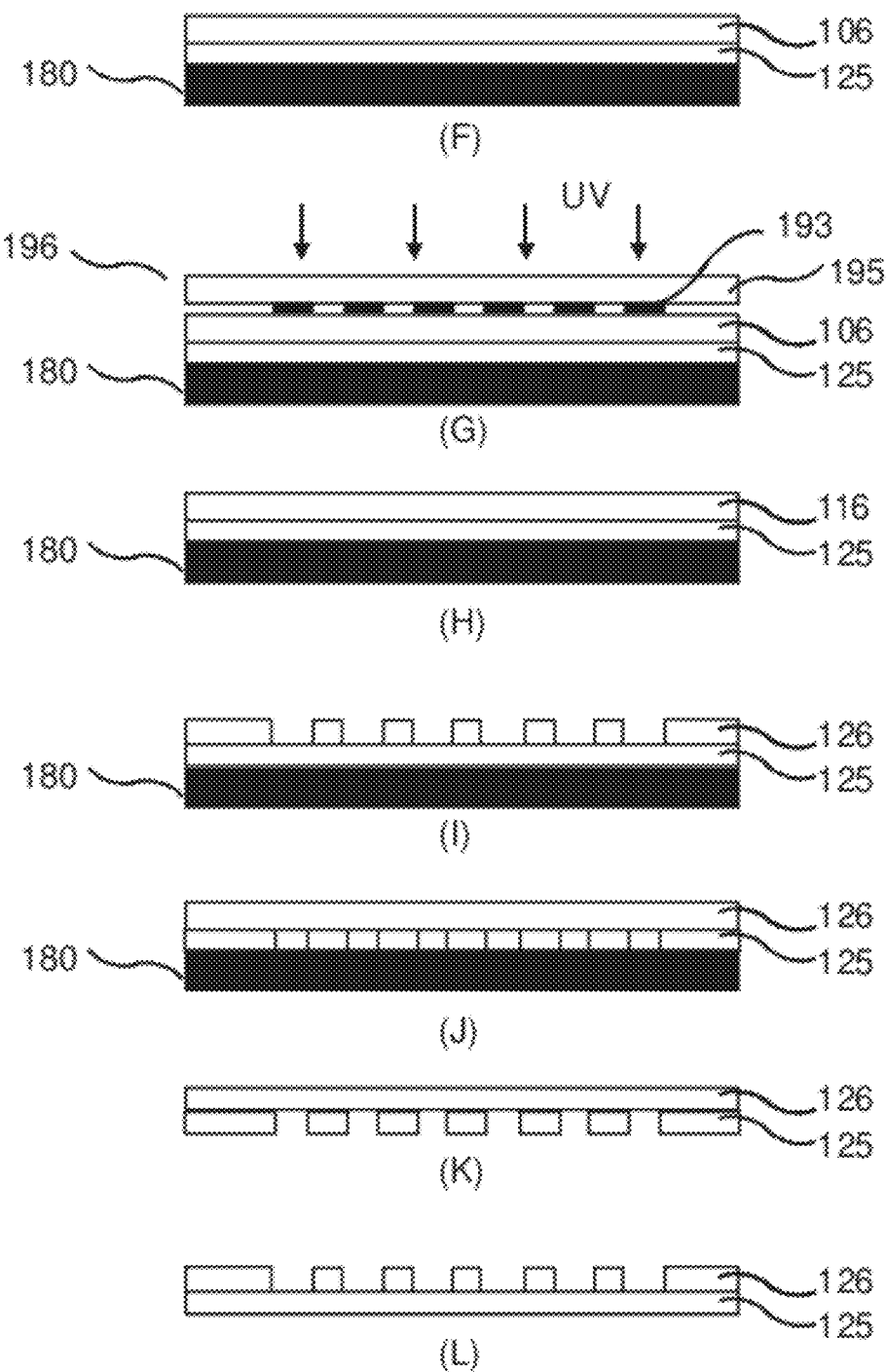
Figure 19:
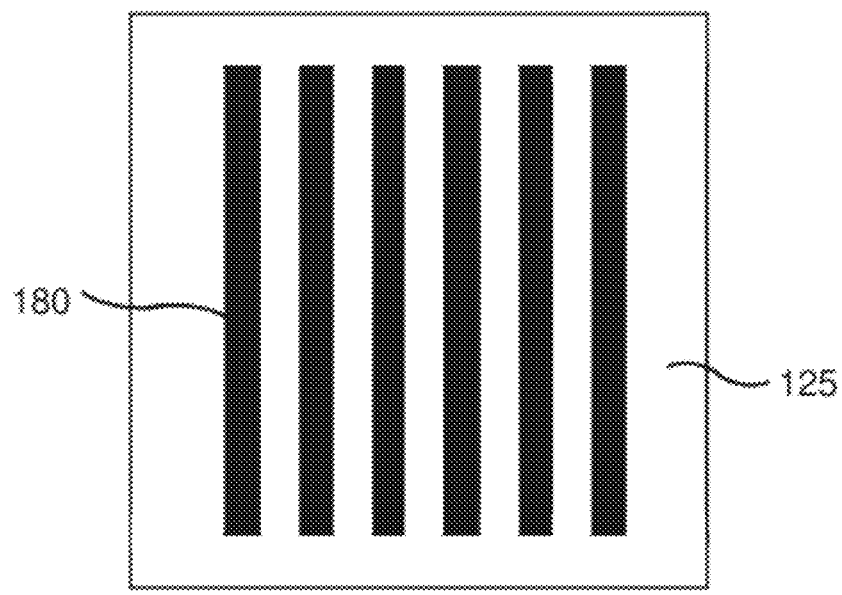
FIGS. 19A-19C.
Figure 19:
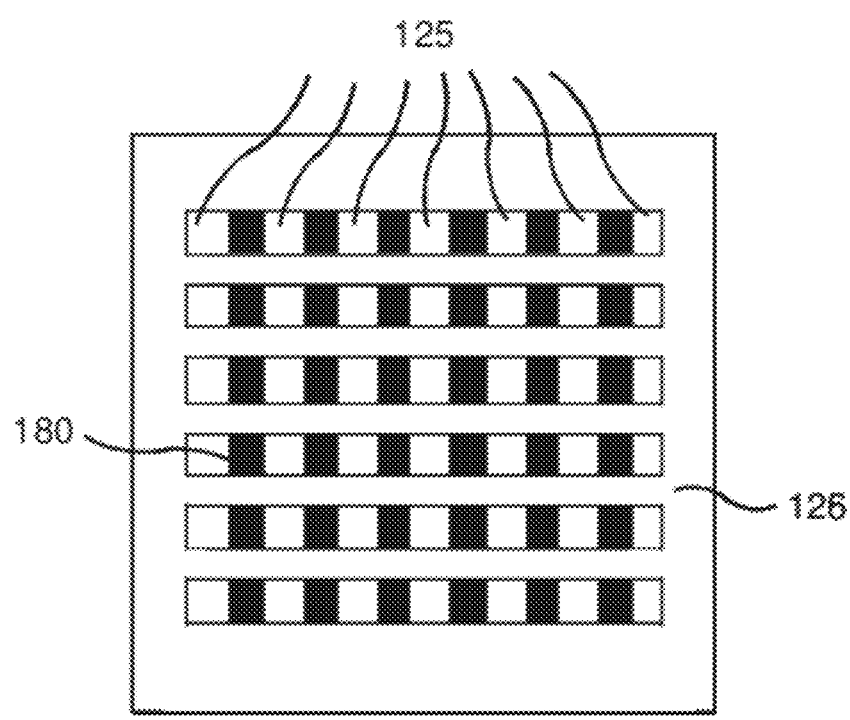
Figure 19:
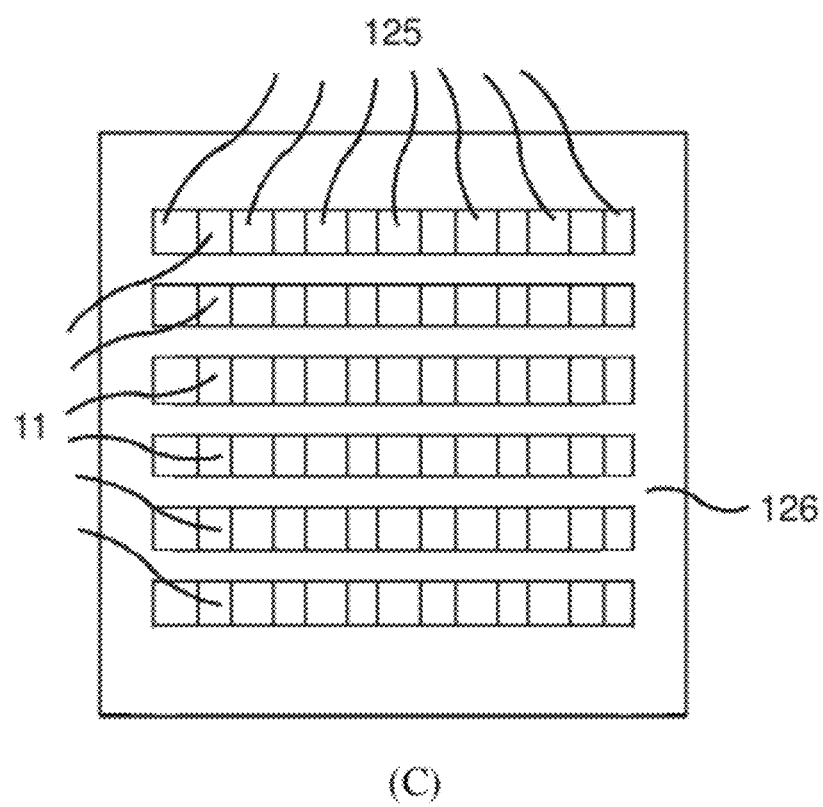

Example 5.A: Microfilter Fabrication Using Two Layers of Dry Films and Copper Release Layer The fabrication steps are described in FIGS. 18A-18L. Steps shown in FIGS. 18A-18E are the same as same as steps shown in FIGS. 2A-2E. The only difference is the layout 194 of the optical mask 196 and the sample of the etched film. The optical mask 196 will consist of strips of metal lines 194. The resultant first layer of the microfilter 125 will consists of trenches that exposes the copper substrate 180 as shown in FIG. 19A.
- a. Laminate negative resist dry film 105 on thin copper foil 180, as shown in FIG. 18A.
- b. Expose the negative resist dry film 105 laminated on copper 180 to UV though the microfilter optical mask, FIG. 18B.
- c. Post bake, FIG. 18C.
- d. Develop the negative resist to form the trenches 11 in film 125, FIG. 18D.
- e. Hard bake (optional), FIG. 18E.

To make the pores, a second negative resist dry film will be added and the fabrication steps are described below.
- f. Laminate a second negative resist dry film 106 on developed film 125, as shown in FIG. 18F.
- g. Expose the negative resist dry film 106 to UV though the microfilter optical mask with mask layout 193, as shown in FIG. 18G. The mask layout consists of strips of metal lines 193 and the line 193 are to be orient perpendicular to the trenches in film 125.
- h. Post bake, FIG. 18H.
- i. Develop the negative resist dry film 116 to form the trenches to obtain patterned second layer of film 126, FIG. 18I.
- j. Hard bake (optional). The side views are shown in FIG. 18I and FIG. 18J, which is rotated by 90° from FIG. 18I. The top view is shown in FIG. 19B.
- k. Etch away copper and release the microfilters to obtain microfilter in two layers, shown in two side views, FIGS. 18K and 18L. The top view is shown in FIG. 19C. The film on top is 126 and the film on bottom is 125. The pores 11 are at the intersections of the trenches in 125 and 126.

Figure 20:
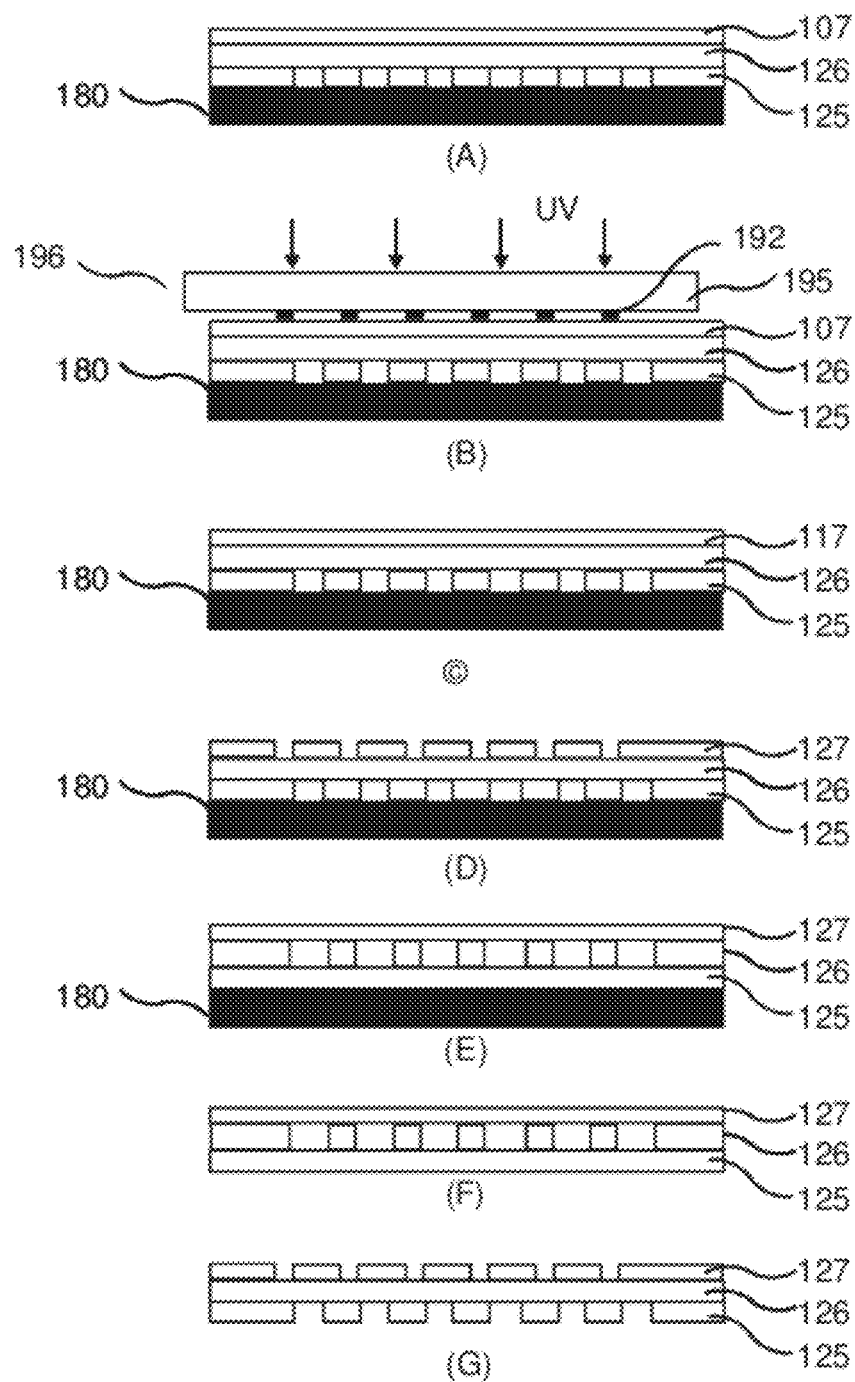
FIGS. 20A-20G.
Figure 21:
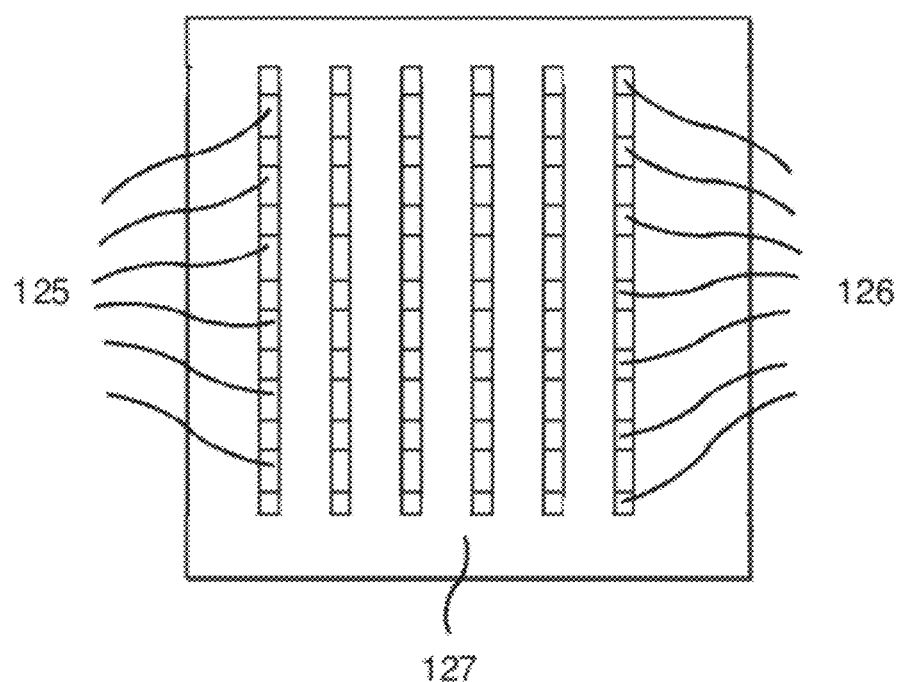
FIG. 21.

Example 5.B: Microfilter Fabrication Using Three or More Layers of Dry Films and Copper Release Layer To make microfilters with long path between entrance and exit of the pores, additional layers of dry film can be used. An example of three layers of dry film is described here. Follow the fabrication steps of FIGS. 18A-18J of Example 5.A to make the first two layers of the filter 125 and 126. Then
  a. Laminate negative resist dry film 107 on developed film 126, as shown in FIG. 20A.
  b. Expose the negative resist dry film 107 to UV though the microfilter optical mask with mask layout 192, as shown in FIG. 20B. The mask layout consists of strips of metal lines 192 and the line 192 are to be orient perpendicular to the trenches in film 126.
  c. Post bake, FIG. 20C.
  d. Develop the exposed negative resist dry film 117 to form the trenches to obtain patterned third layer of film 127, FIG. 20D.
  e. Hard bake (optional). The side views are shown in FIG. 20D and FIG. 20E, which is rotated by 90° from FIG. 20D.
  f. Etch away copper and release the microfilters to obtain microfilter in three layers, shown in two side views, FIGS. 20F and 20G. The top view is shown in FIG. 21. The film on top is 127; the film in between is 126 and the film on bottom is 125. The pores on top are at the intersections of the trenches in films 126 and 127. The pore on the bottom are at the intersections of the trenches in films 125 and 127. Each pore is interconnected to many other pores.

A dry film that is suitable for use for multi-layer microfilters is PerMX™. It is capable of bridging over features already formed on the surface.

The concept using two or more layers of films to make filters can have many variations, such as
  Thickness of films for each layer can be identical, but they do not have to be the same.
  The trenches do not have to be the same on the same layer
  The trenches do not have to be the same on different layers.
  The trenches do not have to be straight.
  The trenches on one layer can be perpendicular to the adjacent layers, but they do not have to be perpendicular.
  The pores on different layers do not have to overlap. This is the case shown in FIG. 21. When the pores on the top and bottom layers do not overlap. filtration path is longer.
  The number of layers can be more than three.

Nanofilter Fabrication by Optical Interference Lithography

In interference lithography, the image is formed by exposing resist to a standing wave formed by the interference of two coherent waves of equal amplitude. In interference lithography, if the optical system is well protected against vibration and air flow, and if the coherence length of a light source is long enough, we can easily generate sinusoidal intensity distribution over a large area, allowing nano-scale lines and dot arrays to be fabricated on a substrate without difficulty.

Three-beam Lloyd's mirror interferometer (J. de Boor, et al Optics Letters 34 (12), 1783 (2009) was used to create in a single exposure a hole pattern with hexagonal symmetry. The period of interference pattern is $\lambda/(1.5 \sin(\theta))$ for 3-beam (hexagonal array), where $\lambda$ is the wavelength of the laser and $\theta$ is the angle between the light beam direction and the perpendicular to the substrate.

A HeCd laser with $\lambda=325$ nm and a typical output power of 30 mW was used for illumination. The light was directed into a spatial filter consisting of focusing lens and a small micron sized pinhole. The distance between the spatial filter and the sample holder was around 1 m, and typical illumination times were 1 to 5 min. The area of the exposed sample is about 4 cm². Position of the mirrors (60×60×5 mm guaranteed 120° symmetry of exposure.

Both positive and negative-tone photoresist can be used, but negative photoresists are more sensitive. Negative-tone imaging also enhances the process latitude for patterning because the hole size can be tuned by exposure dose and various hole diameter can be obtained under the same angle of illumination.

The typical resist thickness was ~10 μm; it is thick enough for easy handling and has relatively good mechanical stability. It is also possible to obtain a frame around nanopores for ease of use and additional mechanical stability of the fabricated membrane. The frame can be obtained by UV-exposure through the mask with the frame pattern.

The invention is the sample preparation method enabling the high-aspect-ratio pore fabrication for both liquid negative photoresist, such as SU-8 and others, and negative dry films, such as PerMX, SUEX and others.

For interference lithography, it is important to have a very smooth surface, to have undisturbed wave front It is also important that there are no scattered or reflected light impinging on the resist. We developed a method that overcomes these problems.

Example Using Liquid Negative Photoresist.

Figure 22:
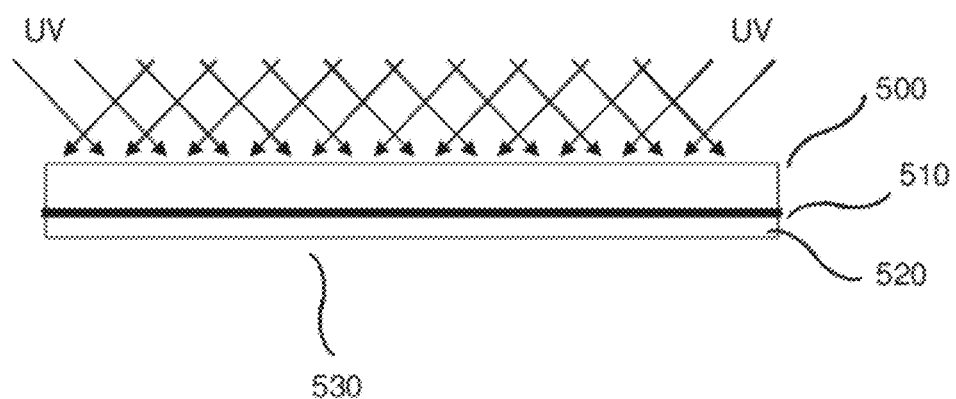
FIG. 22.
Figure 23:
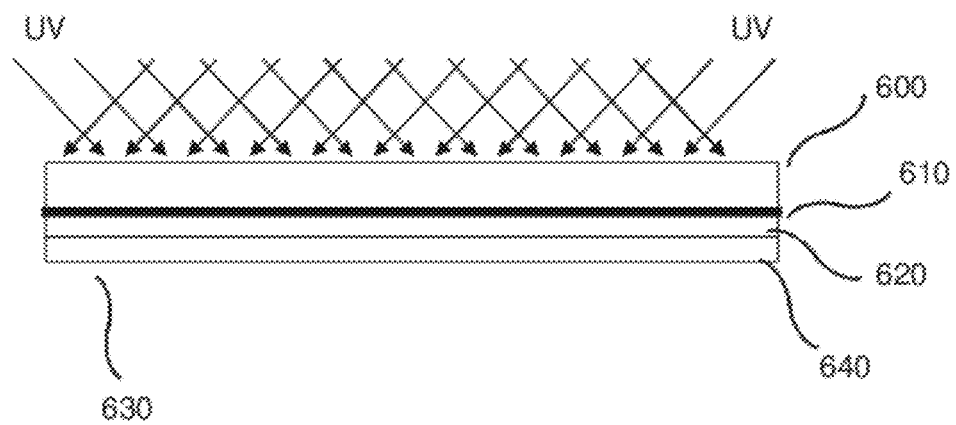
FIG. 23.

The steps of fabrication are described below and shown in FIG. 22.
  a. UV transparent substrates 500 were used, and back-side exposure can be performed. Back-side exposure has an advantage of having an optically flat resist boundary. An example of UV transparent substrate is quartz.
  b. A release layer 510 is coated on the UV transparent substrate. Example of a release material is OMNICOAT (Microchem).
  c. Liquid photoresist 520, such as SU-8 5 (Microchem), is spin coated onto quartz substrate to the desired thickness and prebaked on a hot plate.
  d. The angle of the UV laser light is chosen to obtain the desirable periodicity of the pores. For example, the angle of 18° obtains a pattern with a period of ~700 nm. Interference exposure of the resist was performed from the back-side to obtain the desirable dose.
  e. Exposed sample was post-baked on the hot plate.
  f. Sample was developed in SU-8 developer.
  g. Film was released from the substrate by immersing in SU-8 developer.

If a border or frame is desired, an extra step is needed after Step d. Front-side exposure of the resist through the optical mask with a frame pattern is performed using a mask aligner. This exposure is optional, and was performed for easy handling of a freestanding film.

Example Using Premade Dry Resist Film.

The steps of fabrication are described below and shown in FIG. 22.

a. UV transparent substrates 600 were used, and backside exposure can be performed. Backside exposure has an advantage of having an optically flat resist boundary. An UV transparent substrate is quartz.

b. A release layer 610 is coated on the UV transparent substrate. Example of a release material is OMNI-COAT (Microchem).

c. Laminate the dry film 620 to quartz with the other side still attached to a substrate 630, such as Mylar, d. The angle of the UV laser light is chosen to obtain the desirable periodicity of the pores. For example, the angle of 18° obtains a pattern with a period of ~700 nm. Interference exposure of the resist was performed from the back-side to obtain the desirable dose.

e. Exposed sample was post-baked on the hot plate.

f. Sample was developed in developer.

g. Sample is hard baked.

h. Sample is released from quartz in developer.

Figure 24:
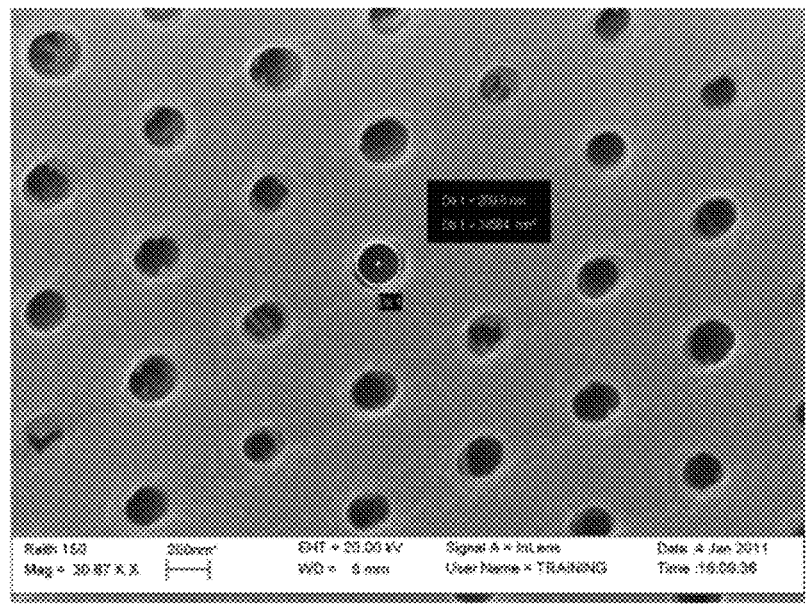
FIG. 24.

FIG. 24 shows SEM of nanofilter using SU-8 showing the pores from the front side. The front side is shown by 530 in FIG. 22.

Figure 25:
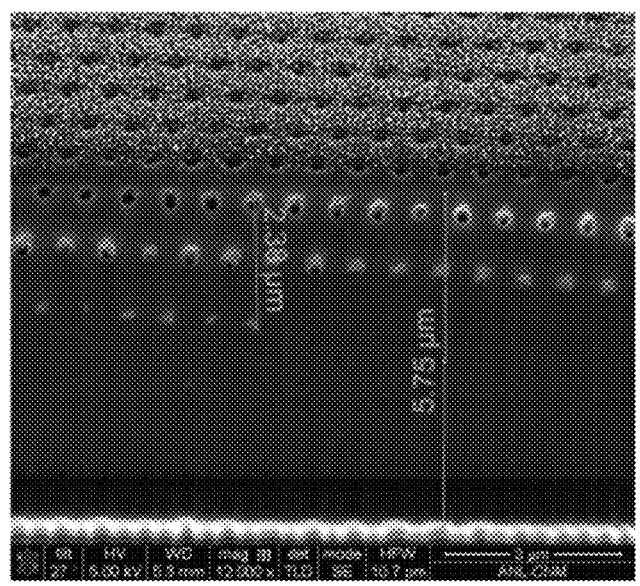
FIG. 25.

FIG. 25 shows cross-sectional SEM image of a processed resist. Focused ion beam milling was used to cut the film at the 25° angle from normal. The geometry factor is 1.15; the pore depth is 2.7 µm. About half thickness of the film was developed. Freestanding film is developing from both sides, and a membrane with holes through the entire resist thickness has been obtained.

Figure 26:
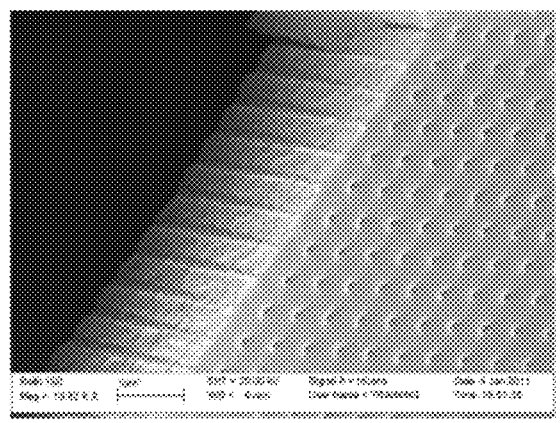
FIG. 26.

FIG. 26 shows ores on the back-side of the developed freestanding 9 micron SU 8 membrane (the cross section shows that the film is fully developed).

Microfilter Feature Options

Microfilter Support.

Figure 17:
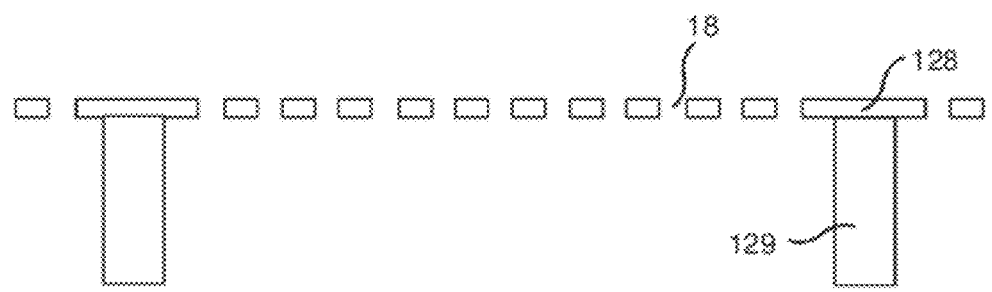
FIG. 17 shows a thin microfilter attached to a more sturdy support.

To provide some microfilter 128 with pores 18 with structural strength, a grid support structure 129 can be implemented as shown in FIG. 17.

Surface Functionalization of Polymeric Microfilters.

It is important to provide the desired surface properties of polymeric microfilters, depending on the potential application.

One modification is to coat the microfilters with a thin layer of parylene.

One surface modification technique of polymer microfilters involves plasma treatment of polymers to activate the surface and graft self-assembled monolayers with a range of functionality including amine, carboxyl, hydroxyl, epoxy, aldehyde, and polyethylene glycol (PEG) groups by using silane chemistry with solution immersion or vapor deposition. For example, grafting PEG-triethoxysilane onto an oxidized polymer renders the surfaces hydrophilic in a controlled manner.

Surface of the polymeric microfilters can also be functionalized with avidin, biotin, protein A, protein G, antibodies, etc.

Microfilter Applications

To prevent breakage of membrane during filtration, thicker polymeric films can be used or support structure as shown in FIG. 17. The support can also be provided separately by the filter holders.

The invention also describes the uses of the precision microfilters. There are a wide variety of applications for microfilters from medical, water filtration, beer and wine filters, pathogen detection, etc.

The present invention provides methods and compositions for isolating and detecting rare cells from a biological sample containing other types of cells.

One application example is for capturing circulating fetal cells in the mother's blood during 11-12 weeks of pregnancy. Fetal cells circulating in the peripheral blood of pregnant women are a potential target for noninvasive genetic analyses. They include epithelial (trophoblastic) cells, which are 14-60 µm in diameter, larger than peripheral blood leukocytes. Enrichment of circulating fetal cells followed by genetic diagnostic can be used for noninvasive prenatal diagnosis of genetic disorders using PCR analysis of a DNA target or fluorescence in situ hybridization (FISH) analysis of genes.

A large application of precision microfilters is for detection of circulating tumor cells in blood. For this application, previous research report utilizing microfilters with orderly arranged pores can only be fabricated with solid parylene by RIE. Here, we can fabricate microfilters with precision ordered pores using a large number of available polymer materials. These materials can have a thin coating of parylene.

The use of microfilter consists of obtaining a blood sample from the patient, which can be in the range of 1-10 ml. The blood is flown through the microfilter. The microfilter can be hold in a filter holder with an inlet, an outlet, by securely holds the filter around the edges. This device can have built in support in the filter holder. It can have gasket above and below the filter.

The blood is pushed through from the inlet. Most cells larger than the pore dimension are retained. Some white blood cells are deformable and can go through pores with smaller dimension than the cell size. The application of enriching circulating fetal cells and tumor cells are based on this principle.

Even though researchers only reported microfilters with pores 7-8 µm in diameter for enriching CTCs, the microfilter pores can be larger for cancer with large cancer cells and can be smaller for cancer with smaller cancer cells.

Microfilters using 10-25 µm thick films can be fabricated by the method described in this invention. Thicker microfilters may provide more structural strength.

One polymer film that is well suited for microfiltration application is PerMX™ 3000 series. Some of the properties that make it suitable for microfiltration for diagnostic application are:

UV sensitive,

Clear,

High tensile strength, 75 Mpa.

Can be pre-laminated to itself and to substrate and

No auto-fluorescence in the visible wavelengths.

Normally, PerMX™ 3000 series is currently used for permanent applications where it is images, cured and left on devices. It is used as an adhesive for microelectronics and packaging, bonding, bumping/pillar applications. (http://www2.dupont.com/WLP/en_US/assets/downloads/pdf/PerMX3000_datasheet.pdf). According to an exemplary implementation of the present invention, PerMX™ 3000 series is utilized for microfilters as free standing film. Variations of these films can also be used without departing from the scope and spirit of exemplary embodiments of the present invention.

The captured CTCs can be enumerated on the microfilters. They can be specifically identified by genomic DNA and fluorescently tagged antibodies for intracellular and surface markers.

The captured CTCs can be subjected to a variety of analysis and manipulations, such as immunofluorescence, cell counting, PCR, fluorescence in-situ hybridization (FISH), immunohistochemistry, flow cytometry, immunocytochemistry, image analysis, enzymatic assays, gene expression profiling analysis, efficacy tests of therapeutics, culturing of enriched cells, and therapeutic use of enriched rare cells. In addition, depleted plasma protein and white blood cells can be optionally recovered, and subjected to other analysis such as inflammation studies, gene expression profiling, etc.

The microfilter can be coated with EpCAM antibody to further retain the CTCs.

The captured CTCs can be cultured directly on the microfilters to increase the number of CTCs and to evaluate the characteristics of CTCs. One example of the rational for culturing the CTCs is to evaluate its expression of disease markers. A simple method to determine the disease marker expression is to coat the surface of channels of the microfilters with capture reagent for the disease marker and later for a fluorescent sandwich assay to specifically identify the disease marker if it is present.

The captured CTCs can be analyzed for DNA, RNA, mRNA and microRNAs expressions for target of interest.

The present invention provides methods and compositions for isolating and detecting rare cells from a biological sample containing other types of cells. In particular, the present invention includes a step that uses a microfabricated filter for filtering fluid samples and the enriched cells can be used in a downstream process such as identifies, characterizes or even grown in culture or used in other ways.

Other applications include enriching stromal cells, mesenchymal cells, endothelial cells, epithelial cells, stem cells, non-hematopoietic cells, etc. from a blood sample and tumor cells in urine.

The present invention provides method and microfilters to capture analytes bound to latex beads or antigen caused particle agglutination whereby the analyte/latex bead or agglutinated clusters are captured on the membrane surface.

The present invention provides method and microfilters for erythrocyte deformability testing. Red blood cells are highly flexible cells that will readily change their shape to pass through pores. In some diseases, such as sickle cell anemia, diabetes, sepsis, and some cardiovascular conditions, the cells become rigid and can no longer pass through small pores. Healthy red cells are typically 7.5 µm and will easily pass through a 3 µm pore membrane, whereas a cell with one of these disease states will not. In the deformability test, a 5 µm membrane is used as a screening barrier. A blood sample is applied and the membrane is placed under a constant vacuum. The filtration rate of the cells is then measured, and a decreased rate of filtration suggests decreased deformability.

The present invention provides method and microfilters for leukocyte/Red blood cell separation. Blood cell populations enriched for leukocytes (white blood cells) are often desired for use in research or therapy. Typical sources of leukocytes include whole peripheral blood, leukopheresis or apheresis product, or other less common sources, such as umbilical cord blood. Microfilters with The present invention provides method and microfilters for chemotaxis applications. Membranes are used in the study of white blood cell reactions to toxins, to determine the natural immunity in whole blood. Since immunity is transferable, this assay is used in the development of vaccines and drugs on white blood cells.

The present invention provides method and microfilters for blood filtration/blood transfusion. Microfilters can be used to remove large emboli, platelet aggregates, and other debris.

The present invention provides method and microfilters for capture of cells and the subsequent culture in the filter cartridge or backflushing.

Because the arrays of precision micro-pores can be fabricated in rolls of polymer resists, it opens up applications that wafer sized microfilters are not able to satisfy. Examples are for water filtration, kidney dialysis, etc.

While the invention has been shown and described with reference to certain exemplary embodiments thereof, it will be understood by those skilled in the art that various changes in form and details may be made therein without departing from the spirit and scope of the invention, as defined by the appended claims and equivalent thereof.

We claim:
1. A method for fabricating a microfilter, the method comprising:
fabricating first strips of trenches on a first layer of a negative resist dry film including:
laminating the first layer of the negative resist dry film to a removable substrate;
exposing the first layer of the negative resist dry film by UV lithography at an angle of a UV laser light from at least two directions with respect to a surface of the first layer of the negative resist dry film to obtain a selected periodicity of pores at an intersection of said UV laser light from said at least two directions;
conducting post bake on the first layer of the negative resist dry film on the removable substrate;
developing the first layer of the negative resist dry film to form the first strips of trenches in a first direction;
fabricating second strips of trenches on a second layer of a negative resist dry film including:
laminating the second layer of the negative resist dry film on the developed first layer of the negative resist dry film;
exposing the second layer of the negative resist dry film by UV lithography;
conducting post bake of the first layer and the second layer of the negative resist dry films on the removable substrate;
developing the second layer of the negative resist dry film to form the second strips of trenches in a second direction;
laminating a third layer of a negative photoresist dry film on the developed second layer of the negative resist dry film;
exposing the third layer of the negative resist dry film by UV lithography;
conducting post bake of at least the third layer of the negative photoresist dry film; and
developing the third layer of the negative photoresist dry film to form third strips of trenches in the first direction;
removing the removable substrate from the first layer of the negative resist dry film; and
forming a freestanding unattached microfilter structure comprising the first, second and third layers of the negative photoresist dry film including micropores defined by the second strips of trenches of the second layer formed in the second direction overlapping the first strips of trenches of the first layer formed in the first direction, and by the third strips of trenches in the third layer formed in the first direction overlapping the second strips of trenches in the second layer formed in the second direction.

2. The method of claim 1, wherein a thickness of the at least one of the first, second and third layers of the negative photoresist dry film is about 10-50 µm.

3. The method of claim 1, further comprising coating the microfilter with at least one antibody.

4. The method of claim 1 wherein the removable substrate comprises a copper foil.

5. The method of claim 1 wherein the removable substrate comprises a foil;
he laminating of the first layer of the negative resist dry film comprises laminating the first layer of the negative resist dry film to a release layer and the foil; and
the removing of the removable substrate from the first layer of the negative resist dry film comprises peeling the negative resist dry films off the release layer.

6. The method of claim 1, further comprising attaching the freestanding unattached microfilter structure to a grid support structure.

7. The method of claim 1, wherein:
the removable substrate comprises a copper substrate;
forming the first and second strips of trenches comprises
forming the first and second strips of trenches on one of the first and second layer perpendicular to strips of trenches on the other of the first and second layer; and
removing the removable substrate comprises removing the copper substrate from the first layer of the negative resist dry film, thereby forming the pores at intersections of the strips.

8. The method of claim 1,
wherein the freestanding unattached microfilter structure consists of the first, second and third layers of the negative photoresist dry film including micropores defined by the second strips of trenches of the second layer formed in the second direction overlapping the first strips of trenches of the first layer formed in the first direction, and by the third strips of trenches in the third layer formed in the first direction overlapping the second strips of trenches in the second layer formed in the second direction.

9. The method of claim 1, wherein the removable substrate comprises a UV transparent substrate.

10. The method of claim 9 wherein the UV transparent substrate is quartz.

11. The method of claim 1, wherein a thickness of the of the at least one of first, second and third layers of the negative photoresist dry film is less than 10 µm.

12. A method for fabricating a microfilter, the method comprising:
fabricating first strips of trenches on a first layer of a negative resist dry film including:
laminating the first layer of the negative resist dry film to a removable substrate;
exposing the first layer of the negative resist dry film by UV lithography;
conducting post bake on the first layer of the negative resist dry film on the removable substrate;
developing the first layer of the negative resist dry film to form the first strips of trenches in a first direction;
fabricating second strips of trenches on a second layer of a negative resist dry film including:
laminating the second layer of the negative resist dry film on the developed first layer of the negative resist dry film;
exposing the second layer of the negative resist dry film by UV lithography at an angle of a UV laser light from at least two directions with respect to a surface of the second layer of the negative resist dry film to obtain a selected periodicity of pores at an intersection of said UV laser light from said at least two directions;
conducting post bake of the first layer and the second layer of the negative resist dry films on the removable substrate;
developing the second layer of the negative resist dry film to form the second strips of trenches in a second direction;
laminating a third layer of a negative photoresist dry film on the developed second layer of the negative resist dry film;
exposing the third layer of the negative resist dry film by UV lithography;
conducting post bake of at least the third layer of the negative photoresist dry film; and
developing the third layer of the negative photoresist dry film to form third strips of trenches in the first direction;
removing the removable substrate from the first layer of the negative resist dry film; and
forming a freestanding unattached microfilter structure comprising the first, second and third layers of the negative photoresist dry film including micropores defined by the second strips of trenches of the second layer formed in the second direction overlapping the first strips of trenches of the first layer formed in the first direction, and by the third strips of trenches in the third layer formed in the first direction overlapping the second strips of trenches in the second layer formed in the second direction.

13. A method for fabricating a microfilter, the method comprising:
fabricating first strips of trenches on a first layer of a negative resist dry film including:
laminating the first layer of the negative resist dry film to a removable substrate;
exposing the first layer of the negative resist dry film by UV lithography;
conducting post bake on the first layer of the negative resist dry film on the removable substrate;
developing the first layer of the negative resist dry film to form the first strips of trenches in a first direction;
fabricating second strips of trenches on a second layer of a negative resist dry film including:
laminating the second layer of the negative resist dry film on the developed first layer of the negative resist dry film;
exposing the second layer of the negative resist dry film by UV lithography;
conducting post bake of the first layer and the second layer of the negative resist dry films on the removable substrate;
developing the second layer of the negative resist dry film to form the second strips of trenches in a second direction;
laminating a third layer of a negative photoresist dry film on the developed second layer of the negative resist dry film;
exposing the third layer of the negative resist dry film by UV lithography at an angle of a UV laser light from at least two directions with respect to a surface of the third layer of the negative resist dry film to obtain a selected periodicity of pores at an intersection of said UV laser light from said at least two directions;

conducting post bake of at least the third layer of the negative photoresist dry film; and developing the third layer of the negative photoresist dry film to form third strips of trenches in the first direction;

removing the removable substrate from the first layer of the negative resist dry film; and forming a freestanding unattached microfilter structure comprising the first, second and third layers of the negative photoresist dry film including micropores defined by the second strips of trenches of the second layer formed in the second direction overlapping the first strips of trenches of the first layer formed in the first direction, and by the third strips of trenches in the third layer formed in the first direction overlapping the second strips of trenches in the second layer formed in the second direction.

* * * * *